US008600774B2

(12) United States Patent
Saidel et al.

(10) Patent No.: US 8,600,774 B2
(45) Date of Patent: Dec. 3, 2013

(54) SYSTEMS AND METHODS FOR EXCHANGING HEALTH CARE CREDITS

(75) Inventors: Andrew M. Saidel, North Potomac, MD (US); David K. Rosen, Guilford, CT (US)

(73) Assignee: Stage 5 Innovation, LLC, Washington, DC (US)

( * ) Notice: Subject to any disclaimer, the term of this patent is extended or adjusted under 35 U.S.C. 154(b) by 16 days.

(21) Appl. No.: 13/273,456

(22) Filed: Oct. 14, 2011

(65) Prior Publication Data
US 2013/0096933 A1 Apr. 18, 2013

(51) Int. Cl.
G06Q 50/00 (2012.01)
G06Q 10/00 (2012.01)

(52) U.S. Cl.
USPC .................................. 705/2; 705/4

(58) Field of Classification Search
USPC ........................................................ 705/2
See application file for complete search history.

(56) References Cited

U.S. PATENT DOCUMENTS

| | | | |
|---|---|---|---|
| 5,819,228 A | 10/1998 | Spiro | |
| 5,937,387 A | 8/1999 | Summerell et al. | |
| 6,269,339 B1 | 7/2001 | Silver | |
| 6,904,336 B2 | 6/2005 | Raines et al. | |
| 7,133,750 B2 | 11/2006 | Raines et al. | |
| 7,541,547 B2 | 6/2009 | McGuire et al. | |
| 7,624,037 B2 | 11/2009 | Bost | |
| 7,801,786 B2 | 9/2010 | Smith et al. | |
| 7,828,205 B2 | 11/2010 | Cronin et al. | |
| 7,925,519 B2 | 4/2011 | Greene | |
| 7,967,731 B2 | 6/2011 | Kil | |
| 8,504,389 B2 | 8/2013 | Saidel et al. | |
| 2002/0077219 A1 | 6/2002 | Cohen et al. | |
| 2002/0123908 A1 | 9/2002 | Ando et al. | |
| 2003/0065561 A1 | 4/2003 | Brown et al. | |
| 2005/0010439 A1 | 1/2005 | Short | |
| 2005/0234742 A1 | 10/2005 | Hodgdon | |
| 2006/0064331 A1 | 3/2006 | Odermott et al. | |
| 2006/0111944 A1 | 5/2006 | Sirmans, Jr. et al. | |
| 2007/0192195 A1 | 8/2007 | Asmar et al. | |
| 2008/0109263 A1 | 5/2008 | Clark et al. | |
| 2008/0162496 A1 | 7/2008 | Postrel | |
| 2008/0255873 A1 | 10/2008 | Berkley | |
| 2009/0018870 A1 | 1/2009 | Weishaar | |
| 2009/0063197 A1 | 3/2009 | Lisle | |
| 2010/0211416 A1* | 8/2010 | Frank et al. | 705/4 |
| 2010/0235196 A1 | 9/2010 | Bartholomew, III et al. | |

(Continued)

OTHER PUBLICATIONS

Baicker, Policy Watch: Trade Adjustment Assistance, 2004, American Economic Association, vol. 18, No. 2, pp. 239-255.*

(Continued)

*Primary Examiner* — Tran Nguyen
(74) *Attorney, Agent, or Firm* — MH2 Technoloy Law Group, LLP

(57) ABSTRACT

Systems and methods for exchanging health care credits are described. Health care credits are transferable units of value representing good health, an improvement in health, or maintenance of health by an individual. The health care credits may be bought, sold, exchanged for goods and services, gifted or otherwise conveyed from one owner to another. Also disclosed are exchanges and markets for buying, selling, and trading health care credits, as well as derivative securities. The derivative securities or products are based on either the flow of health care credits through the system, or on health care information, which may have been generated to implement health care credit awards.

108 Claims, 9 Drawing Sheets

(56) References Cited

U.S. PATENT DOCUMENTS

| | | |
|---|---|---|
| 2011/0015960 A1 | 1/2011 | Martin et al. |
| 2011/0087503 A1 | 4/2011 | Desai |
| 2011/0137784 A1 | 6/2011 | Douglas |
| 2011/0160544 A1 | 6/2011 | Hayter |
| 2011/0161255 A1 | 6/2011 | Short |

OTHER PUBLICATIONS

Volpp et al., "Redesigning Employee Health Incentives—Lessons from Behavioral Economics", New England Journal of Medicine, 365;5, NEJM.org, Aug. 4, 2011, pp. 388-390 http://www.nejm.org/doi/fulll/10.1056/NEJMp1105966, accessed Aug. 16, 2012, 3 pages.

Volpp et al., "Health Affairs—P4P4P: An Agenda for Research On Pay-For-Performance for Patients", Health Affairs, 28, No. 1, 2009, pp. 206-214 http://content.healthaffairs.org/content/28/1/206.full, accessed Aug. 16, 2012, 10 pages.

Volpp et al., "A test of financial incentives to improve warfarin adherence", BMC Health Services Research, 8:272, 2008, pp. 1-6 http://www.biomedcentral.com/1472-6963/8/272/, accessed Aug. 16, 2012, 6 pages.

Baicker et al., Policy Watch: Trade Adjustment Assistance, American Economic Association, 2004, vol. 18, No. 2, pp. 239-255.

Notice of Allowance dated Jun. 7, 2013, U.S. Appl. No. 13/486,427, filed Jun. 1, 2012, pp. 1-49.

International Search Report and Written Opinion dated Mar. 13, 2013, PCT Application No. PCT/US2012/59457, filed Oct. 10, 2012, pp. 1-18, published by the WIPO.

Author Unknown, Int'l Search Report and Written Opinion for Int'l Appl. No. PCT/US2012/59486 (filed Oct. 10, 2012) dated Jan. 4, 2013, pp. 1-10; published on the Internet by WIPO.

"Life Points", http://www.cdphp.com/members/life_points.aspx, accessed Jan. 5, 2012, 1 page.

"GEHA—Member Web Services—Overview/Demo", http://www.geha.com/webenablement/member_demo.asp, accessed Jan. 5, 2012, 3 pages.

GEHA, "Keynotes" newsletter, Fall 2011, accessed Jan. 5, 2012, 4 pages.

Unitedhealthcare, "UnitedHealthCare's 'UnitedHealth Personal Rewards' Program Gives Consumers Customized Road Maps to Healthier Lifestyles", http://www.uhc.com/news/2010_news_release_archive/unitedhealth_personal_reward_program.htm, accessed Jan. 5, 2012, 4 pages.

Discovery Vitality, Annexure 1: Points for each benefit and status, 10 pages http://www.discovery.co.za/discovery_za/web/pdfs/vitality/summary_of_points.pdf (accessed Sep. 25, 2012).

Discovery Vitality, Main rules for Discovery Vitality, 10 pages http://www.discovery.co.za/discovery_za/web/pdfs/vitality/summary_of_vitalitys_rules.pdf (accessed Sep. 25, 2012).

* cited by examiner

SYSTEMS AND METHODS FOR EXCHANGING HEALTH CARE CREDITS

RELATED APPLICATIONS

This application is related to the following commonly-assigned, co-pending U.S. patent applications: Ser. No. 13/273,430, entitled "SYSTEMS AND METHODS FOR PROCESSING THE REDEMPTION OF HEALTH CARE CREDITS" by the same inventors; and Ser. No. 13/273,366, entitled "SYSTEMS AND METHODS FOR PROVIDING HEALTH CARE CREDITS TO SUBSCRIBERS" by the same inventors, both of which were filed on the same day as the present application, and the entire disclosures of which are incorporated herein by reference.

FIELD

This invention generally relates to systems and methods for health care operations. More particularly, this invention relates to platforms and techniques for monetizing, transferring, and exchanging credits representing health care related actions and outcomes.

BACKGROUND

Health insurance is insurance that pays for all, or a portion, of the expenses incurred by an individual for health-related care, such as medical care, medications, etc. Generally, a health insurance company or government entity that provides health insurance (in either case referred to as a health insurer) provides health care benefits to an individual as specified in an insurance policy or insurance plan, in exchange for periodic payments or premiums. By modeling the risk of health care expenses for a group of people that the insured belongs to (e.g., Caucasian males aged 40-50), the insurer can calculate a premium that provides enough assets to pay for the health care benefits specified in the insurance plan, should the need arise. Health insurance does not generally reward behavior that maintains or improves health, but rather, penalizes people with deteriorating health or pre-existing conditions by raising premiums or excluding coverage.

Because health care is expensive, health care insurance is also expensive. As a consequence there are many disenfranchised people who do not have health care insurance, do not have enough health care insurance, or do not have the correct health care insurance, because they cannot afford it. Moreover, because they cannot afford health care, the uninsured and underinsured often avoid seeking health care until or unless they develop acute symptoms or chronic illnesses. Often, medical problems that would have been easily and inexpensively solved in the early stages have become complex and expensive to solve by the time the uninsured and underinsured seek care. Even thought non-emergency care providers often will not treat the uninsured and underinsured because they cannot pay, uninsured and underinsured patients nonetheless obtain expensive health care treatments in emergency rooms that legally cannot deny them care. The cost of caring for the uninsured and underinsured is passed on in higher prices to insurance companies and insured patients.

A fairly new development in health care is the practice of evidence-based medicine or evidence-based health care. Evidence-based health care seeks to provide treatment, services, and medications for a health problem based on the best currently available evidence regarding treatment of the health problem. The evidence may be obtained from sources that range from highly scientific, published clinical trials to conventional wisdom. Evidence-based health care is most effective in those areas of medical practice that have been frequent subjects of scientific studies, usually from clinical trials; i.e., those areas that have accumulated the most evidence that is accessible to medical practitioners.

By systematically and scientifically identifying effective, ineffective, and harmful treatments, evidence-based health care may reduce health care costs by reducing expenditures on ineffective and harmful treatments.

There are several novel improvements that may be made to conventional health care payment systems and health insurance, as well as improvements to evidence-based health care.

SUMMARY

Systems and methods consistent with the present disclosure create and utilize health care credits. Health care credits may be issued to individuals by a health insurer, including a governmental health insurer, or other entity, and the individual may store and manage their health care credits using a specialized account. The individual may transfer health care credits from their account to other accounts for various reasons. In addition, the individual may sell the health care credits for cash, including selling them on a specialized exchange or marketplace. Investment vehicles that are based on the movement of health care credits, or based on health care information (which may in some embodiments be gathered incidental to health care credit management) may be created and traded, including derivative investment vehicles.

Various embodiments include systems, computerized methods, and computer-readable storage media for managing health care credits, which perform operations and actions that may include receiving health care credits, wherein the health care credits represent good health, or improvement in health, or maintenance of health; storing the health care credits in an account controlled by an entity, for example an individual; receiving an instruction from the entity; and deducting, using the computing system, health care credits from the account according to the instruction.

Other embodiments include systems, computerized methods, and computer-readable storage media for exchanging health care credits, which perform operations and actions that may include receiving an offer, from an entity, to exchange health care credits; identifying a reciprocal offer that matches the offer to exchange the health care credits; exchanging the health care credits for proceeds according to the offer and the reciprocal offer; and providing the proceeds to the entity. In some such embodiments, the health care credits represent good health, or improvement in health, or maintenance of health.

Yet other embodiments include systems, computerized methods, and computer-readable storage media for administering a health care derivative, which perform operations and actions that may include creating the health care derivative, wherein the health care derivative has a value that depends upon fulfilling a condition related to health care; collecting data related to health care and the condition; determining, from the data, whether the condition has been fulfilled; and adjusting the value of the health care derivative according to whether the condition has been fulfilled.

BRIEF DESCRIPTION OF THE DRAWINGS

The accompanying drawings, which are incorporated in and constitute a part of this specification, illustrate embodiments and implementations of the present disclosure and together with the description, serve to explain the embodiments and implementations. Wherever convenient, the same reference numbers may be used to refer to the same or like features.

In the drawings.

DETAILED DESCRIPTION

Overview

Figure 1:
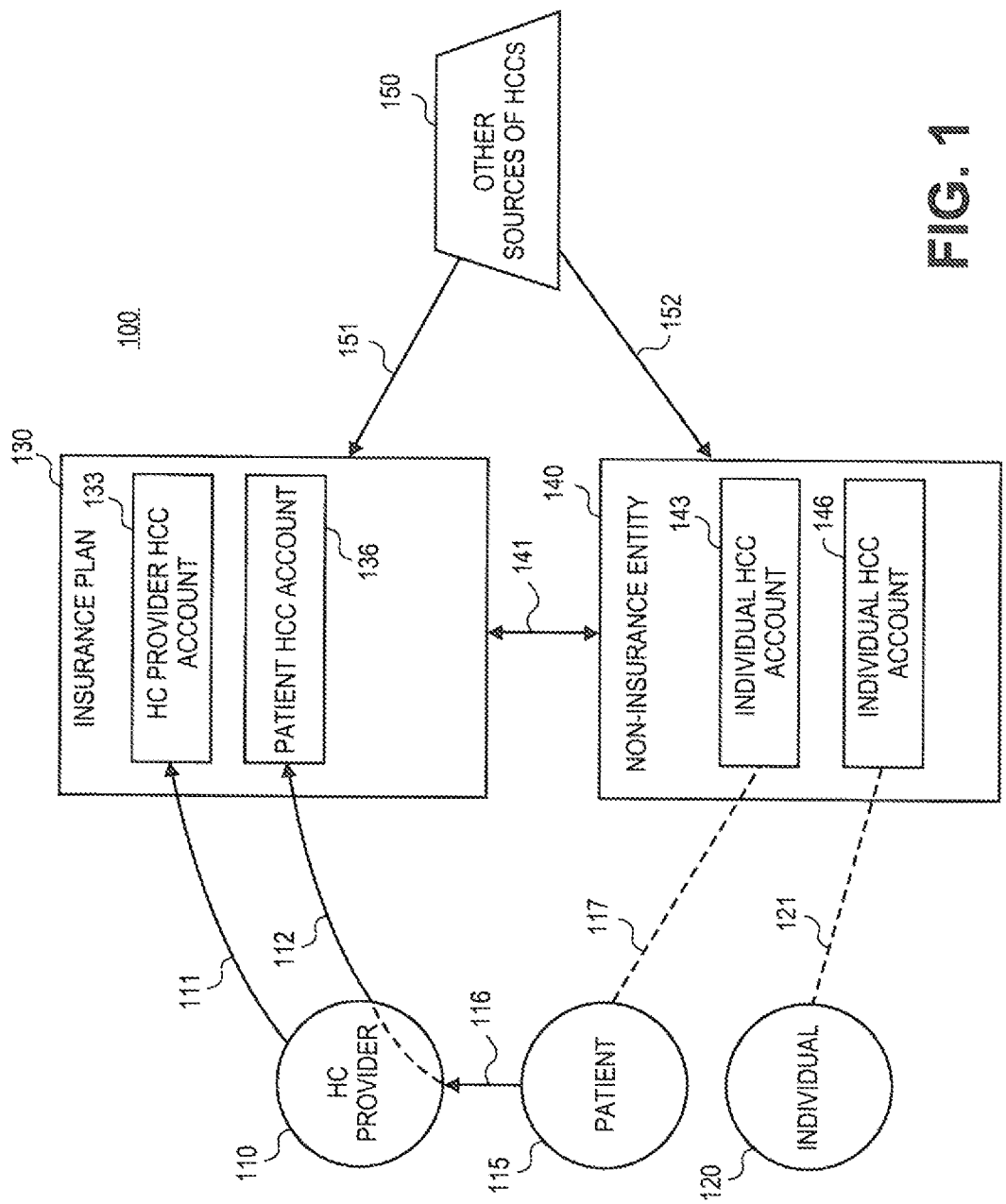
FIG. 1 is a block diagram of exemplary health care credit accounts, consistent with the principles of the invention.

Various embodiments consistent with the present disclosure create and utilize Health Care Credits (HCCs). Generally, a "health care credit," as used herein, can refer to an award, reward, or other type of credit provided to an individual that rewards the individual for good health and/or healthy behaviors, as well as incentivizes the individual to maintain and/or improve their health level. In various embodiments, health care credits have intrinsic value because they can be used and accepted as a payment for health care services received by the individual, thus monetizing the health care credits or using the credits as a sort of currency. Further, the health care credits can be freely transferrable, sellable, conveyable, and/or the like, to other individuals, subscribers, and/or entities and exchanged for goods and services. Still further, the health care credits can be securitized. Moreover, the health care credits can be bought, sold, and exchanged in a market-type environment comprising authorized agents, brokers, channels, exchanges and/or other entities or components.

Various implementations of HCCs proved several advantageous improvements to current health care systems. For example, awarding HCCs to individuals (e.g., patients) and/or health care providers (e.g., physicians) provides a direct incentive to create, maintain or improve health for these participants in the health care system.

For example, a patient may be awarded HCCs for achieving an improved health level outcome, such as a reduced cholesterol level or body mass index (BMI). For another example, an insured individual may be provided with HCCs for engaging in health-benefiting behaviors, including commercial behaviors, such as joining a health club or gym, purchasing particular food items or health-benefiting products, shopping at particular establishments, such as health food stores or organic restaurants, etc. In the same vein, eligibility for an award of HCCs may be used to promote health-benefiting products and services.

In addition to patients, a physician may earn HCCs for formulating the regimen that the patient successfully followed to produce the improved health level outcome, (e.g., increased exercise and a prescription for a cholesterol-reducing medication).

HCCs may also incentivize behaviors in the preventative health area, such as awarding HCCs to patients who engage in healthy behaviors (e.g., exercise, regularly take medication, etc.), even if the patient's health level does not necessarily show improvement, but instead remains the same (e.g., cholesterol level does not increase, or a chronic condition, such as diabetes, does not worsen over a significant time period, such as 6 months).

Health insurance providers, including insurance companies, governmental health insurers, and supplemental health insurance providers (e.g., Aflac®, AARP™), realize benefits for using HCCs as incentives because their subscribers/members/insureds achieve better health, resulting in their using less health care services overall and using more inexpensive preventive care services while requiring fewer expensive acute, chronic, and emergency care services, all of which reduce costs for the insurer.

Another improvement provided by HCCs is that they monetize improved health outcomes and behaviors as an independent economic value, which opens up a range of uses, including opportunities to earn future health care insurance coverage during present periods when an individual is healthy. For example, young, healthy people, who typically need few if any health care services during their early years of coverage, may be awarded HCCs while young and achieving high levels of good health, and they may save the HCCs for later use, "spend" the HCCs right away, or convert them to cash. For instance, young healthy people, who generally pay much more in health insurance premiums than they incur in health care costs during most of their lives, may exchange HCCs with their insurer immediately to reduce their health care insurance premiums or sell them for cash.

For an example regarding saved HCCs, later in life, when health problems start to affect the formerly young people, they may use saved HCCs to reduce their later, more expensive insurance premiums, or to pay for health care services not covered by insurance. Another advantageous effect of awarding HCCs for healthy behavior in young individuals is an overall reduction in health care treatments throughout the entire health care system as young people are incentivized early on to engage in healthy behaviors, which makes it less likely they will develop medical problems and unhealthy habits later in life.

Another improvement provided by various embodiments of HCC systems is in providing techniques and mechanisms for transferring improved health outcomes between health systems. For example, HCCs earned with one health care insurer may be saved or exchanged and used with a different health care insurer because the health improvements and benefits for an individual, which are represented by the HCCs earned by that individual, remain with the individual, thus reducing costs for a health insurer, regardless of which insurer the individual is contracting with at any particular time.

Yet another improvement provided by various embodiments of HCC systems is in providing techniques and mechanisms for tracking and trading on specific health care treatments and interventions. For example, the data collected, stored, and analyzed in connection with treatments, patient behaviors and activities, and measured health outcomes in order to determine amounts of HCCs to award to each individual patient may be combined with data from many other individuals and analyzed to determine the effects of the health care treatments and interventions on the group. Some embodiments may provide a novel tradable contract or security (e.g., a derivative security) having a value related the effects of specific health care treatments or interventions.

Health Care Credit Accounts

As noted above and explained in greater detail in the related applications which are incorporated by reference into this application, in various embodiments health care credits are valuable currency-like entities that may be earned or awarded for beneficial health-related behaviors and positive and/or improved health-related outcomes. In various embodiments, HCCs may be exchanged for value, for example to offset health insurance premiums, saved for use later, exchanged for either health-related or non-health-related goods or services, traded or sold through a broker, etc. In most embodiments, accounts are provided to hold, transfer, and exchange HCCs.

FIG. 1 is a block diagram of exemplary health care credit accounts, consistent with the principles of the invention. In the embodiment of a system of accounts 100 shown in FIG. 1, an insurance company or insurance plan 130 may establish and manage a health care provider HCC account 133 and a patient HCC account 136 that are used by a health care provider 110 (e.g., a physician) and a patient 115, respectively. In some embodiments, insurance plan or company 130 may be a public or private health insurance company, a government-sponsored health care insurance program, such as Medicare, Medicaid, CHIP, military health care programs (TriCare), etc., a state health care program, a supplemental insurance company, such as Aflac® or AARP™, (which supplements Medicare), or the like. As discussed in the related applications referenced above, insurance plan 130 may place HCCs in account 133 for HC provider 110 according to data 111 provided by HC provider 110 documenting beneficial health regimens and positive health outcomes related to patient 115 under the care of HC provider 110. Similarly, insurance plan 130 may place HCCs in account 136 for patient 115 according to data 112 provided by HC provider 110 documenting beneficial health regimens and positive health outcomes related to patient 115 under the care of HC provider 110. In the embodiment shown, data 112 is based on data 116 provided HC provider 110 by patient 115.

Accounts 133 and 136 may also received HCCs from sources other than insurance plan 130. For example, as shown in FIG. 1, HCCs may be transferred 151 to accounts 133 and 136 from other sources of HCCs 150, which includes sources such as HCC accounts maintained by other insurance companies, HCC brokerage accounts, employers, etc., from which HCCs may be earned, awarded, bought, inherited, gifted, given as an employer match, given as a credit-usage or other promotional reward, or otherwise conveyed.

As shown, a non-insurance entity 140, such as a brokerage, investment firm, bank, or company set up specifically to provide HCC accounts, may establish and manage HCC accounts, such as an individual HCC account 143 and an individual HCC account 146. As shown in this example, a person having no relationship to any insurance company, (such as Individual 120), may nonetheless have a health care credit account, (such as individual HCC account 146). As represented by dashed lines 117 and 121 in the embodiment shown, individual HCC account 143 is controlled by and maintained for patient 117, and individual HCC account 146 is controlled by and maintained for individual 120.

Accounts 143 and 146 may receive/transfer 141 HCCs from/to insurance plan 130 according to the directions of patient 115 and individual 120, respectively. Similarly, accounts 143 and 146 receive/transmit 152 HCCs from/to other sources of HCCs 150 according to the directions of patient 115 and individual 120, respectively. In some embodiments, HCC accounts 133, 136, 143, 146, may have properties similar to electronic bank accounts, such as earning interest, in the form of HCCs, on HCCs held in the account, automatic transfer of HCCs to offset a periodic bill, such as a monthly insurance premium, etc.

One of ordinary skill in the art will recognize that system 100 depicted in FIG. 1 is an exemplary, generalized illustration and that components and features may be added to, removed from, or modified within system 100 without departing from the principles of the invention. For one example, patient HCC account 136 may be removed, such that the only account associated with patient 115 is individual HCC account 143, and such that HCCs awarded to patient 115 by insurance plan 130 are deposited directly into individual HCC account 143 by insurance plan 130. For another example, in some embodiments, a single health care account may be provided for a group of individuals (e.g., a family) instead of only a single individual. In such embodiments, positive health behaviors by any member of the group (e.g., eating better and losing weight or reducing BMI by an obese child) may earn HCCs that may be used by other members of the group (e.g., used by a parent of the obese child to reduce the cost of medications).

Figure 2:
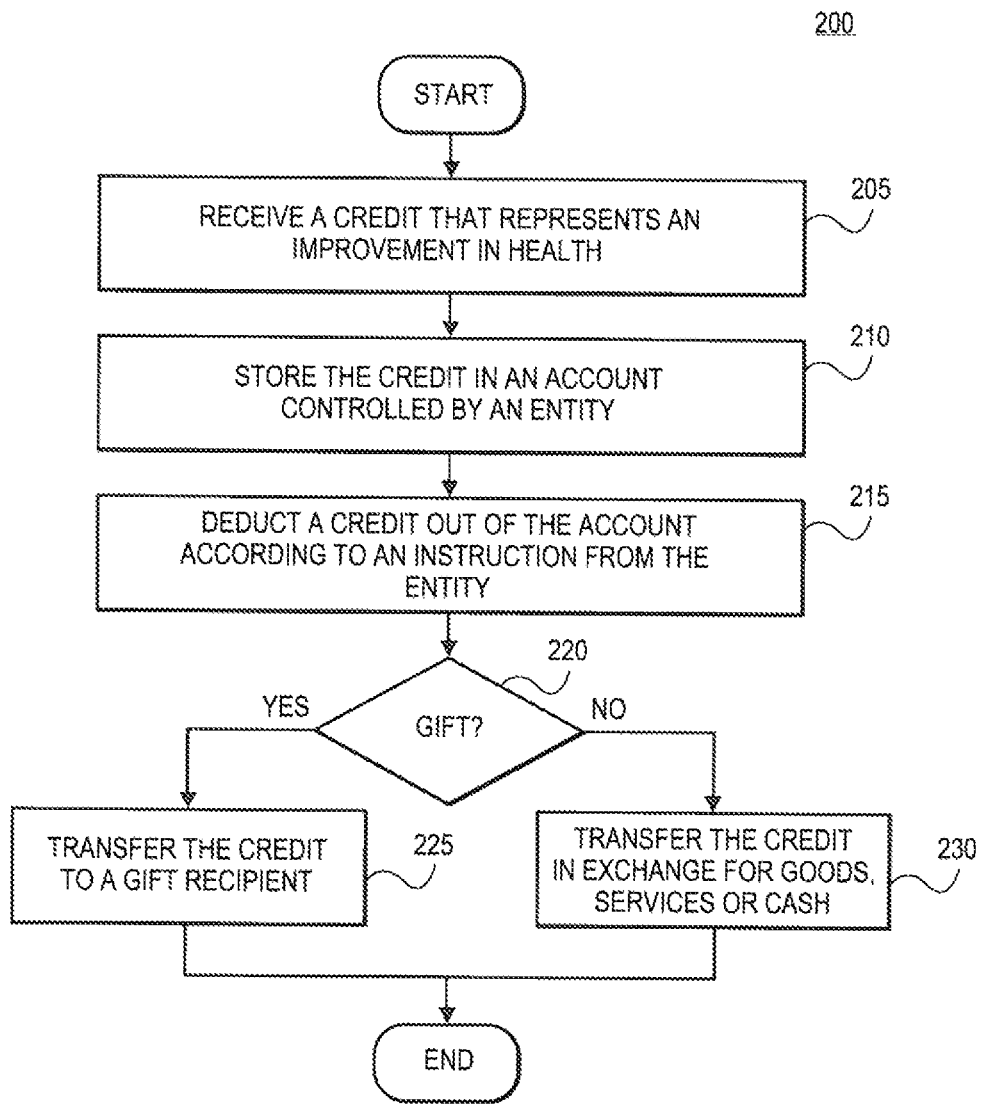
FIG. 2 is a flowchart of an exemplary process for managing a health care credit account, consistent with the principles of the invention.

FIG. 2 is a flowchart of an exemplary process 200 for managing a health care credit account, consistent with the principles of the invention. In some embodiments, process 200 may be implemented using a computing system by an entity functioning as a HC account provider and/or an HC account servicer, such as an insurance company 130 or a non-insurance entity 140, for example a broker, as shown in FIG. 1. In the embodiment shown in FIG. 2, process 200 begins with receiving a credit that represents an improvement in health (stage 205), such as a HCC as described previously. In various embodiments, the credit may transferred or transmitted from a HCC account, (such as accounts 133, 136, 143, or 146 of FIG. 1), or the credit may be earned from, or awarded, originated, or created by an entity that seeks to reward and incentivize beneficial health-related behavior and care, such as an insurance company, government agency, or employer. In various implementations of this stage, the credit may be received in the form of electronic signals or electronic digital data.

At stage 210, process 200 stores the credit, which represents an improvement in health, in an account controlled by an entity. In some embodiments, the account may be a health care provider HCC account 133 controlled by an HC provider 110, a patient HCC account 136 controlled by a patient 115, or an individual HCC account 146 controlled by an individual 120, or the like, as shown in FIG. 1. In various embodiments, the entity may be an individual, including an insured individual enrolled in a health insurance plan, or a legal entity, such as a trust, corporation, non-profit organization, etc. In various implementations, the credit may be stored in the form of electronic digital data on a computer readable medium.

At stage 215, process 200 deducts a credit from the account according to an instruction from the entity that controls the account. For one example with reference to FIG. 1, non-insurance entity 140 may deduct a credit(s) from individual HCC account 143 according to an instruction 117 from patient 115, so that the credit(s) can be used to reduce a health insurance premium owed to insurance plan 130. In various implementations, the credit, (which represents an improvement in health), may be deducted by reducing an electronic value representing the amount of HCCs held in the account.

Process 200 next transfers the deducted credit(s) according to the instruction from the entity controlling the account and ends. In the embodiment shown, process 200 first determines whether the credit is a gift (stage 220). If the credit is a gift, (stage 220, Yes), then process 200 transfers the credit to a gift recipient (stage 225), such as to the account of a family member. For example, a healthy husband may transfer credits he has accumulated to the account of his wife who requires an expensive medication whose cost has exceeded the maximum benefit limit of her health insurance policy, allowing the wife to use the credits to offset the continuing cost of the medication. Thus, the wife obtains a benefit from the husband's good health (and corresponding lack of expense to the husband's health insurer) as represented in the form of the husband's health care credits. This is another exemplary improvement over conventional health care systems wherein one individual cannot benefit in any way from another individual's healthy behaviors and outcomes.

If the credit is not a gift, (stage 220, No), then process 200 transfers the credit to entity that provides, in exchange, goods, services (e.g., a reduction to a health insurance premium), cash, or the like to, or for the benefit of, the entity that controls the account (stage 230). In various implementations, the credit(s), (which represents an improvement in health), may be transferred in the form of electronic signals or electronic digital data.

One of ordinary skill in the art will recognize that process 200 depicted in FIG. 2 is an exemplary, generalized illustration and that stages and features may be added to, removed from, or modified within process 200 without departing from the principles of the invention. For one example, a stage may be added to process 200 wherein deducted credits are removed or disposed of, instead of being transferred to another account, such as in the case where a credit held in an account provided by an insurance company (e.g., patient HCC account 136 provided by insurance company 130), is used to reduce a health insurance premium charged for a policy underwritten by that same insurance company.

Health Care Credit Exchange

As explained in the related applications, various embodiments of health care credit systems award something of value, HCCs, to individuals (patients, insureds, etc.) for beneficial health-related behaviors and outcomes. This is an improvement over conventional health care systems because an individual's health level and health-related behaviors do not significantly financially impact an individual in conventional systems. For example, when an already insured individual gains weight or ceases exercising or ceases taking physician-described medication in a conventional health care system, these actions do not increase the individual's premium or reduce some other financial benefit. Conversely, when an already insured individual reduces their BMI, reduces cholesterol level, or starts an exercise program, these actions do not decrease the individual's premium or increase some financial benefit. Individuals have little incentive to be healthy, because their costs in a conventional system are essentially the same whether they act in a healthy manner or not.

In contrast, health care credit systems consistent with the present disclosure may immediately discourage unhealthy actions by reducing or eliminating the amount of HCCs awarded to the individual. If the individual is using HCCs to reduce their premiums, then this effectively raises their premiums. Moreover, various embodiments may further improve over conventional health care systems by providing exchanges or markets where HCCs may be bought and sold, which effectively allow sellers to convert HCCs into cash. In such embodiments, reducing or eliminating HCC awards discourages unhealthy behaviors because the affected individuals suffer the financial loss of not having sufficient HCCs to either exchange for health services or cash, or exchange, trade, or sell on an exchange.

Figure 3:
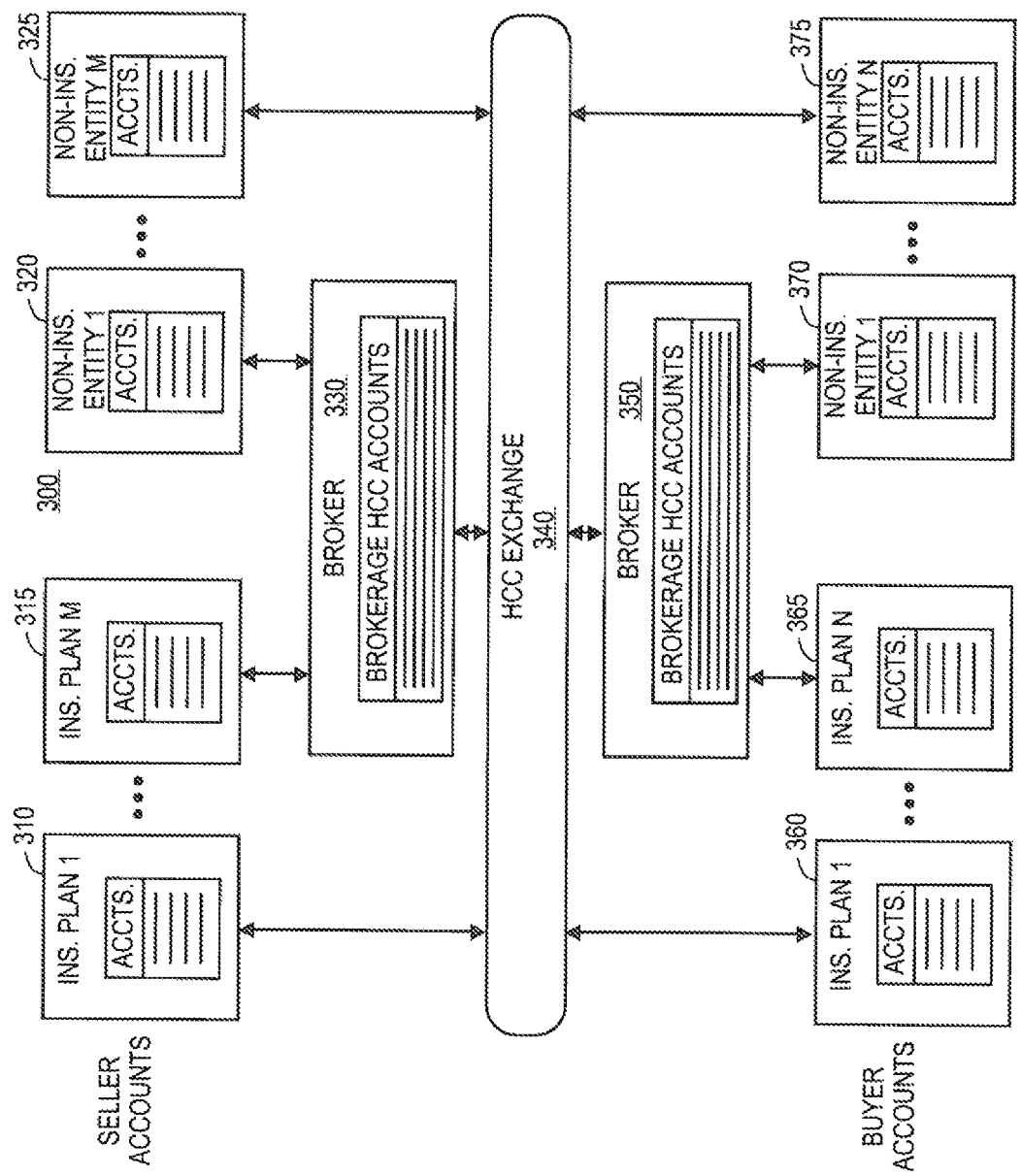
FIG. 3 is a block diagram of an exemplary system for exchanging health care credits, consistent with the principles of the invention.

FIG. 3 is a block diagram of an exemplary system 300 for exchanging health care credits, consistent with the principles of the invention. In the embodiment shown, system 300 includes a HCC exchange 340, which is a market that is designed for the sale and purchase of health care credits issued by an entity or entities. In various embodiments, issuing entities may be health insurance companies, government agencies, or the like. In various embodiments, HCC exchange 340 may sell and buy HCCs and/or securities derived from HCCs. In various embodiments, HCC exchange 340 may be implemented as a computerized market to trade health care credits, which represent an improvement in health. In some embodiments wherein the HCCs issued by different health insurers are essentially the same regardless of issuer, HCC exchange 340 may be implemented in a manner similar to the NASDAQ™ market for trading stocks. In other embodiments wherein the HCCs issued by different health insurers have different intrinsic values and/or are valued differently depending upon issuer, HCC exchange 340 may be implemented in a manner similar to the FOREX™ market for trading currencies.

As shown, sellers of HCCs may have HCC accounts provided and maintained by insurance plans 310, 315 and/or by non-insurance entities 320, 325. In some instances, sellers may utilize a broker 330 to interact with HCC exchange 340, for example by transferring HCCs from an insurance plan account 315 or a non-insurance entity account 320 into a brokerage account 330, from which the HCCs may be sold on exchange 340. In various embodiments, brokerage account 330 may also include a cash component for managing money received in exchange for HCC credits.

Similarly, buyers of HCCs may have HCC accounts provided and maintained by insurance plans 360, 365 and/or by non-insurance entities 370, 375. In some instances, buyers may utilize a broker 350 to interact with HCC exchange 340, for example by transferring HCCs or cash from an insurance plan account 365 or a non-insurance entity account 370 (e.g., a bank account) into a brokerage account 350, from which the HCCs may be bought via exchange 340. In various embodiments, brokerage account 350 may include both a cash component for managing money paid in exchange for HCC credits, and an HCC credit component for receiving and storing purchased HCCs.

In the embodiment shown in FIG. 3, sellers and buyers may interact directly with HCC exchange 340 without using a broker. As shown, sellers having accounts with an insurance plan 310 or a non-insurance entity 325 may offer HCCs for sale on HCC exchange 340, where the HCCs may be bought by buyers having accounts with an insurance plan 360 or a non-insurance entity 375. In such embodiments, HCC accounts 310, 325, 360, and 375 may include both a cash component for managing money paid/received in exchange for HCC credits, and an HCC credit component for transmitting, receiving and/or storing purchased HCCs. In some such embodiments, HCC exchange 340 may be implemented as a computerized online trading platform for HCC, which represent an improvement in health, in a manner similar to the eBay™ trading platform.

One of ordinary skill in the art will further recognize that system 300 depicted in FIG. 3 is an exemplary, generalized illustration and that components and features may be added to, removed from, or modified within system 300 without departing from the principles of the invention. For example, one of ordinary skill will recognize that seller accounts 310, 315, 320, 325 may also be used to buy HCCs on HCC exchange 340, and similarly buyer accounts 360, 365, 370, 375 may also be used to sell HCCs on HCC exchange 340. For another example, one of ordinary skill will also recognize that seller accounts 310, 315, 320, 325 and buyer accounts 360, 365, 370, 375 are not limited to being owned or controlled only by individual persons. In some embodiments HCC accounts may be owned or controlled by corporations or other legal entities, which may, for example, wish to purchase HCCs that can be awarded to their employees, or by foundations or other organizations that wish to purchase HCCs for donation to other individuals or groups.

Figure 4:
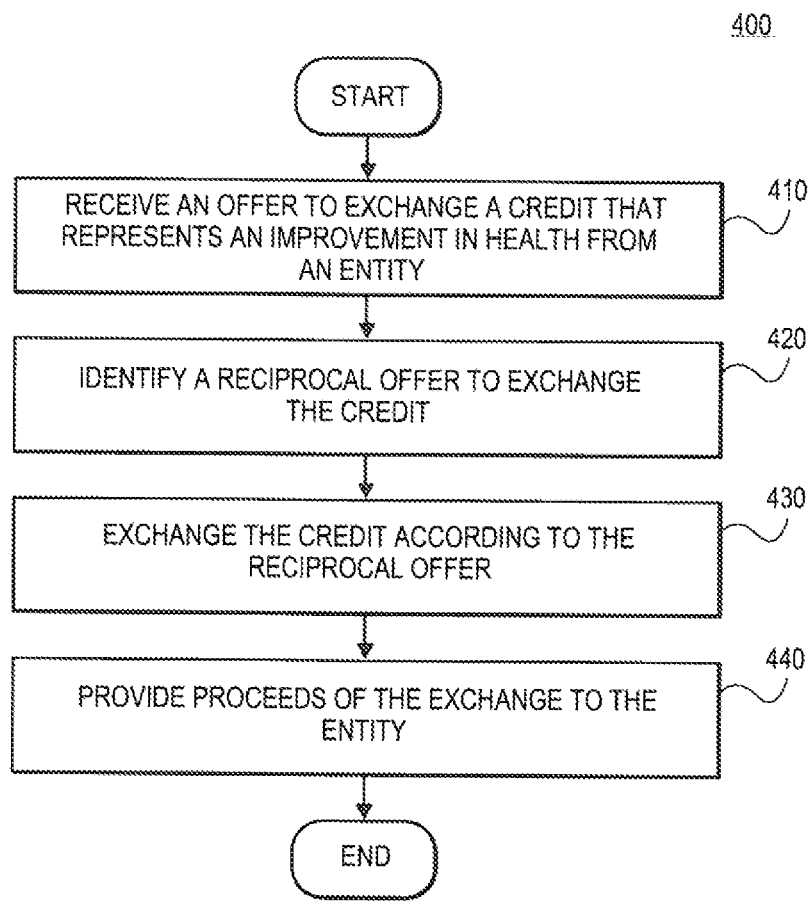
FIG. 4 is a flowchart of an exemplary process for exchanging health care credits, consistent with the principles of the invention.

FIG. 4 is a flowchart of an exemplary process 400 for exchanging health care credits, consistent with the principles of the invention. In some embodiments, process 400 may be implemented using a computing system by an entity providing a market to buy and/or sell HCCs, such as HCC exchange 340, as shown in FIG. 3. In the embodiment shown in FIG. 4, process 400 begins with receiving, from an entity, an offer to exchange a credit(s) that represents an improvement in health, (e.g., an HCC). For example, the offer may be an offer to sell a HCC for a specified minimum amount of cash, an offer to buy a HCC for a specified maximum amount of cash, an offer to sell a HCC for the current market price, an offer to buy a HCC for the current market price, or an offer to swap a specified quantity of one type of HCC for a specified quantity of another type of HCC, (e.g., swap 1.0 HCC issued by Blue Cross Blue Shield for 2.5 HCCs issued by Medicare). In various embodiments, the entity may be an individual that has a HCC account, such as HCC accounts 310, 325 or brokerage account 330. In various implementations, the offer to exchange a credit(s) may be received in the form of electronic signals or electronic digital data representing a buy order or a sell order.

At stage 420, process 400 identifies a reciprocal offer(s) to exchange the credit that represents an improvement in health. For example, if process 400 has received an offer to sell 100 HCC for $1.00 each at stage 410, stage 420 may identify one or more offers to buy 100 HCC for at least $1.00 each. In various embodiments, the identification of a reciprocal offer(s) may be implemented by a computing system that matches buy and sell orders according to price, quantity, and other factors.

In various implementations, there may be no reciprocal offer that matches a newly received offer to exchange HCCs and/or the offer to exchange may be an offer to buy or sell HCCs at the current market price. In either case, stage 420 may determine that the appropriate reciprocal offer is a pending offer that is nearest to the price desired by the entity, or the pending offer that is nearest in price to the last completed exchange of the same type of HCC credit (e.g., the last completed trade on a HCC exchange 340).

In some embodiments, HCCs created by different health insurers may have different characteristics, which may cause them to have different values from each other, intrinsically and/or according to their market prices on a market administered by an HCC exchange 340 implementing process 400. For example, consider the case where a first insurer, for instance TriCare insurance, awards HCCs to its insureds such that 100 TriCare HCCs may be exchanged for a $100 reduction in an insured's TriCare insurance premium, and/or exchanged for goods and services from vendors that TriCare has contracted with at a rate of one dollar per TriCare HCC. Consider further a second HCC insurer, for instance Kaiser Permanente™, that awards HCCs to its insureds such that 100 Kaiser HCCs may be exchanged for a $50 reduction in an insured's Kaiser insurance premium and/or exchanged for goods and services from vendors that Kaiser has contracted with at a rate of 75 cents per Kaiser HCC. In some such embodiments, there may also be differences in how many HCCs each insurer awards for the same or similar healthy outcomes or actions by its insureds. Competing insurers may use these and other characteristics of their HCC programs to attract customers.

In such a case, the best reciprocal offer on the market identified by stage 420 for exchanging Kaiser HCCs for Tri-Care HCCs may be an offer to exchange 1.5 Kaiser HCCs for 1 TriCare HCC, or to exchange 2.0 Kaiser HCCs for 1 TriCare HCC, both of which reflect the relative intrinsic values of the HCCs. Or, the exchange rate on the market may vary greatly from the relative intrinsic values of the HCCs due to the relative supply and demand of the two types of HCCs in this example. Similarly, individuals offering to sell the two types of HCCs for cash may be subject to the price set by the market based on supply and demand for each of the two types of HCCs, analogous to foreign currency exchanges.

In other embodiments, HCCs created by different health insurers may have substantially uniform characteristics, regardless of the insurer that issued them. For example, all insurers may allow its insureds to exchange their HCCs on a one-to-one dollar basis for a reduction in a health insurance premium. In some such embodiments, HCCs may be fungible when traded on a market administered by an HCC exchange 340 implementing process 400. In such embodiments, the primary type of market transaction may be exchanging HCCs for cash, where the reciprocal offers (stage 420) are at price determined by the market based on supply and demand for HCCs overall, analogous to stock exchanges wherein an HCC is a security like a share of stock.

As shown in the embodiment of FIG. 4, process 400 next exchanges the credit according to the reciprocal offer (stage 430). Continuing the previous example with respect to this stage, process 400 may deduct 100 HCC from the account (e.g., insurance-plan-managed account 310, non-insurance-entity-managed account 325, or brokerage account 330) of the entity that submitted the sell offer for 100 HCC at $1.00 each, and deduct $100 for the account(s) (e.g., insurance-plan-managed account 360, non-insurance-entity-managed account 375, or brokerage account 350) of the entity(ies) that submitted the reciprocal buy offer(s) of $100 for 100 HCC.

Process 400 then provides the proceeds of the exchange to the entity that transmitted the original offer (stage 440) and then ends. Again continuing the previous example, process 400 may transmit the $100 deducted from the account(s) of the entity(ies) that submitted the reciprocal buy offer(s) of $100 to the entity that transmitted the original sell offer referenced in stage 410.

One of ordinary skill in the art will recognize that process 400 depicted in FIG. 4 is an exemplary, generalized illustration and that stages and features may be added to, removed from, or modified within process 400 without departing from the principles of the invention. For example, a stage may be added to process 400 wherein the proceeds of the exchange are provided to the entity associated with the reciprocal offer (e.g., the buyer that fills a sell order is provided with the HCCs that were purchased).

Health Care Tracking Data and Derivatives

Health care credit systems consistent with the present disclosure provide improved health data gathering and management, which fits well with evidence-based health care practices, and has other novel uses. In various embodiments, to determine whether and how many HCCs to award to individuals, insurers or other HCC administrators or awarders analyze health care data provided by the treating health care provider (e.g., physician). In some embodiments, this same data may be used for various other purposes in addition to administering HCC awards.

For example, the health care data may be used to track over time and evaluate health care treatment regimens and outcomes, including with respect to specific demographic patient groups. Such tracking data may be used to identify marginally effective and ineffective treatment regimens and discourage their use among health care providers, which would provide another improvement over current health care system wherein health care providers are often rewarded based on the amount of treatments they provide (i.e., they are paid per treatment), regardless of effectiveness. In some embodiments, such tracked information may be used as the basis for a derivative security having a value that is directly related to a specific health care outcome and that provides a novel way to monetize health care treatments.

Figure 5:
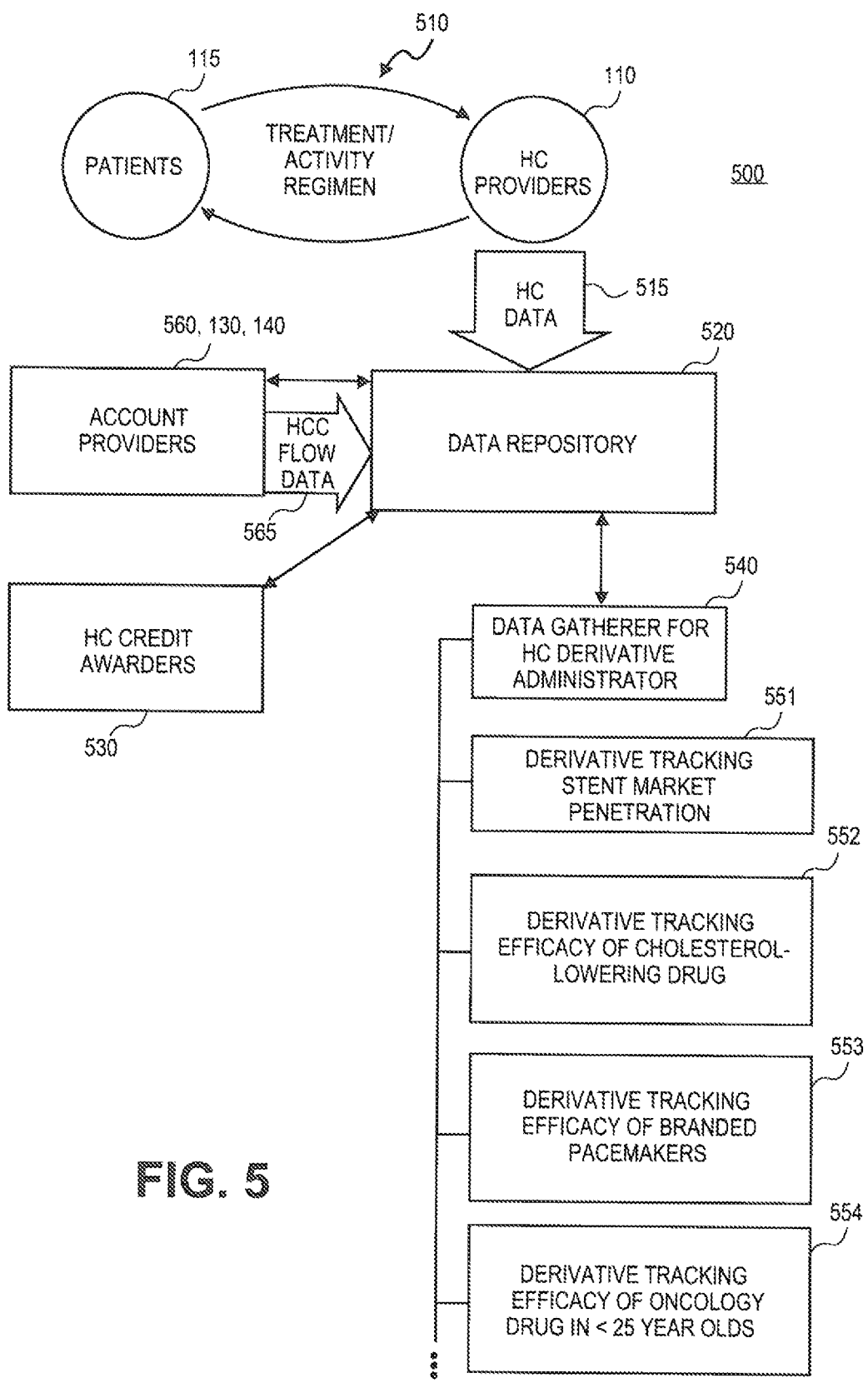
FIG. 5 is a block diagram illustrating an exemplary system for managing data and providing derivative securities related to health care information, consistent with the principles of the invention.

FIG. 5 is a block diagram illustrating an exemplary system 500 for managing data and providing health care derivative securities related to health care information, consistent with the principles of the invention. In various embodiments, a health care derivative may be a security whose price or value is dependent upon or derived from one or more underlying "assets," where the assets are in the form of accurate, current information relating to health care problems, treatments, outcomes, effectiveness, usages, and the like. In some embodiments, the derivative itself may simply be a contract between two or more parties that specifies its value at a future date dependent upon condition(s) of the underlying information. The value of a derivative at any point in time before its expiration is determined by fluctuations in the underlying data with respect to desired conditions—in this case by the changes and content of the underlying health care data—and the market demand. In various embodiments, a health care derivative may be tradable on an exchange or over the counter.

As shown in the embodiment of FIG. 5, health care providers 110 may implement a treatment regimen or health care activity regimen 510 with patients 115, as described in more detail in the related applications.

As the treatment regimen 510 is ongoing, health care provider 110 gathers health care data 515 documenting the patient 115, the health characteristics and/or problem(s), the treatment(s), the outcome(s), etc. In various embodiments, data documenting the patient may include information regarding characteristics such as race, sex, age, height, weight, address, occupation, family history, habits, social history, and the like. In various embodiments, data documenting the patient's health characteristics or problems may include information describing the problem(s) currently being treated (heart disease, cancer, broken bone, migraine headaches, high cholesterol, high BMI, etc.) including baseline and continuing measurements (e.g., artery blockage measurements, tumor size and growth, fracture healing, headache frequency and intensity, blood pressure, cholesterol level, etc.), and the like. In various embodiments, data documenting the patient's treatment regimen may include information describing medications and usages, surgeries or other procedures, appliances used (e.g., stents, etc.), therapy routines, diet, exercise, and the like. In various embodiments, data documenting the patient's outcome(s) may include information describing the result of each treatment, for example, cured, artery blood flow increased 70%, fracture 50% healed, headache frequency reduced 10%, cholesterol lowered by 30%, and the like.

As shown in the embodiment of FIG. 5, health care provider 110 provides health care data 515 to a data repository 520. In various embodiments, data repository 515 may be implemented by a database server or other computing system for maintaining and accessing data.

As shown, account providers 560, such as insurance plan 130 or non-insurance entity 140, also provide data to data repository 520, such as health care credit flow data 565. In some embodiments, health care credit flow data 565 includes information describing transfers of HCCs from one account to another and describing the accounts involved, as well as information regarding HCCs exchanged for goods, services, etc., and the entities involved. In such embodiments, health care credit flow data 565 may indicate, for example, the amount of HCCs that are being sold for cash, the amount of HCCs that are being exchanged for goods and services of contracted vendors, the amount of HCCs that are being exchange for insurance premium reductions, and the like.

Also as shown, health care credit awarders 530 are connected to, and may access, the data in data repository 520. In various embodiments, health care credit awarders 530 include insurance plans/companies 130, which may award HCCs to individuals, such as patients 115, as an incentive to act in a health beneficial manner and for achieving positive health outcomes, as explained in detail in the related applications. Health care credit awarders 530 may read and analyze HC data 515 stored in data repository 520 to determine whether patients 114 have engaged in rewardable activities and/or achieved positive health outcomes. In various embodiments, health care credit awarders 530 may also read and analyze HC data 515 stored in data repository 520 to determine whether HC providers 110 (e.g., physicians) have engaged in rewardable activities (e.g., provided effective treatment regimens to patients 115) and/or achieved positive health outcomes for patients.

In some embodiments where health care credit awarders 530 are insurance companies, they may read and analyze HC data 515 stored in data repository 520 to determine which treatments and regimens produce beneficial results for patients, and which do not, or are less effective than others. This information, in turn, may inform policy coverage decisions by an insurer. For example, an insurer may remove coverage (i.e., not reimburse) for a drug that is not working, according to the information in HC data 515, or an insurer may refuse to cover implantation of a certain, more-expensive brand of pacemaker, if that pacemaker does not achieve results superior to a less expensive brand, according to the information in HC data 515.

In the embodiment shown, a HC derivate administrator 540 is also connected to, and may access, the data in data repository 520. In various embodiments, HC derivate administrator 540 may create, issue, administer, sell, and/or buy HC derivatives whose performance and value are based on underlying HC data 515. As noted above, HC derivatives may be embodied as securities or contracts that track health care outcomes. In an investment sense, HC derivatives provide a far more granular and precise way to invest in and trade on differentiated health care devices, medications, treatments, techniques, etc., in comparison to health care stocks. HC derivatives also provide the opportunity for brokerages and investment houses to create futures and options trades based on underlying health care devices, medications, treatments, techniques, etc.; i.e., futures and options based on the predicted value of a HC derivative.

In the embodiment shown, HC derivative administrator 540 has created and is managing four exemplary derivatives 551-554. HC derivatives 551-554 may be designed and implemented to achieve almost any financial objective based on underlying health care information. In general, HC derivatives may be designed and implemented to provide a profit or payout if specific health-related characteristics and events, as indicated by the underlying HC data 515, turn out to be the way the issuer expects (e.g., move in a given direction, stay in or out of a specified range, reach a certain level or goal, etc.).

For example, HC derivative 551 may be designed to provide leverage related to the market penetration of a specific stent, such that a small market penetration as tracked and indicated by the underlying HC data 515 (e.g., 2% of all stents used will be ACME Corp. model 123A stents 18 months from now), will cause a large difference in the value of HC derivative 551 (e.g., derivative 551 will pay 30 times its issue price in 18 months if the market penetration goal is reached; and otherwise it will be worthless).

For another example, HC derivative 552 may track the efficacy of a new cholesterol lowering drug in African American males, as documented and indicated by the underlying HC data 515, and provide a payout such that, after 12 months of usage, if the new drug lowers overall cholesterol an average of 0-10% in the African American male demographic group, then HC derivative 552 pays nothing; if the new drug lowers overall cholesterol an average of 10.1-25%, then derivative 552 pays 1.5 times its purchase price; if the new drug lowers overall cholesterol an average of 25.1-50%, then derivative 552 pays 2.5 times its purchase price; and if the new drug lowers overall cholesterol an average of 50.1% or more, then HC derivative 552 pays 4 times its purchase price.

For another example, HC derivative 553 may be designed to track the efficacy of two specific brands of pacemakers relative to each other, as indicated by the underlying HC data 515, such that, after 24 months of usage, if Brand A pacemakers have required fewer repairs, adjustments, and replacements than Brand B pacemakers, then the derivative pays three times its purchase price, and otherwise, it pays nothing.

For yet another example, HC derivative 554 may be designed to track the efficacy of a specific oncology drug in a specific age demographic relative to another age demographic, as indicated by the underlying HC data 515, such that, after 24 months of treatment with the oncology drug, if the remission rate for patients 25 years old and younger is 0-15% higher than the remission rate for patients older than 25 years, then the derivative pays nothing; and if the remission rate for patients 25 years old and younger is 15.1% or more higher than the remission rate for patients older than 25 years, then the derivative three pays times its purchase price.

One of ordinary skill in the art will recognize that system 500 depicted in FIG. 5 is an exemplary, generalized illustration and that components and features may be added to, removed from, or modified within system 500 without departing from the principles of the invention. For example, one of ordinary skill will recognize that the examples of HC derivatives 551-554 are illustrative only, and many other health care derivatives are possible within the scope of the invention, including health care derivatives whose payouts are expressed in terms other than as a multiple of the purchase price. For another example, system 500 may be modified so that third parties (not shown), including additional HC derivative creators and insurance companies, may be connected to data repository 520 and allowed to access, mine, and analyze HC data 515 for various purposes, including creating additional HC derivatives and shaping health insurance coverages.

Figure 6:
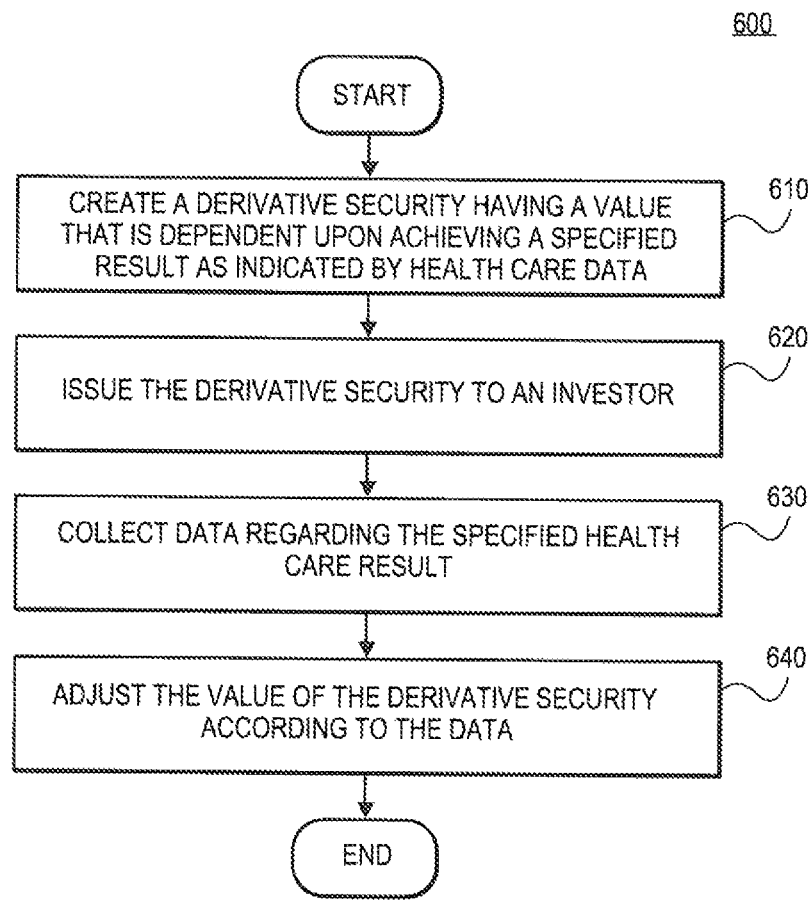
FIG. 6 is a flowchart of an exemplary process for managing a derivative security related to health care credits, consistent with the principles of the invention.

FIG. 6 is a flowchart of an exemplary process 600 for managing a derivative security related to health care and/or health care credits, consistent with the principles of the invention. In some embodiments, process 600 may be implemented using a computing system by an entity that is creating and/or managing derivates that are based on health care treatment and outcome data, such as HC derivative administrator 540, as shown in FIG. 5. In the embodiment shown in FIG. 6, process 600 begins with creating a derivative security having a value that is dependent upon achieving or fulfilling a specified result or condition as indicated by health care data (stage 610). For example, as noted above with respect to FIG. 5, HC derivatives (such as HC derivatives 551-554) may be created such that they increase or decrease in value, or pay out a specified amount, if specific health-related characteristics and events, as indicated by the underlying HC data 515, turn out to be the way the derivative creator expects (e.g., move in a given direction, stay in or out of a specified range, reach a certain level, etc.). In other words, the value of a HC derivative may be tied to a condition(s) that is discernable from health care data and HCC flow data that is generated and collected incidental to providing health care services to individuals and/or tied to whether/how that condition(s) is fulfilled or achieved. In various embodiments, creating the derivative may include specifying a definite time(s) for achieving the specified result(s) and specifying a definite payout(s) if the specified result(s) are achieved at the specified time(s).

At stage 620, process 600 issues the derivative security to an investor(s). In some embodiments, this stage may be implements by selling or trading the HC derivative security either on a regulated exchange, such as the Chicago Board of Trade, on a custom HC exchange, such as HC 340 of FIG. 3, or off the exchanges, directly between the different counter-parties.

Next, process 600 collects data regarding the specified health care result that underlies the derivative (stage 630). In various embodiments, the data collection of stage 630 may be ongoing over the life of the derivative, as new health care data regarding relevant treatments, outcomes, etc. is generated by patients and health care providers over time. In some embodiments, stage 640 may be implemented by retrieving data from data repository 520, as shown in FIG. 5.

At stage 640, process 600 adjusts the value of the derivative security according to the data collected in stage 640 and then ends. For derivatives that feature a final payout at a specified ending date, this stage may involve analyzing the health care data collected in stage 630 as of the final payout date and determining whether, or which, payout conditions were met. For example, consider again the example of HC derivative 551 discussed above with respect to FIG. 5, wherein the derivative was created to pay 30 times its issue price if 2% of all stents used are ACME Corp. model 123A stents during a period ending 18 months after creation of HC derivative 551. In this example, stage 640 involves accessing and analyzing HC data 515 to determine the total number of stents employed during the relevant 18 month period and the number of ACME Corp. model 123A stents among that total. Then, stage 640 calculates whether the number of model 123A stents is equal to or greater than 2% of the total, and if so, adjusts the values of HC derivative 551 to be 30 times its issue price. Or, if the calculation shows the number of model 123A stents is less than 2% of the total, then stage 640 adjusts the value of HC derivative 551 to be zero.

In various embodiments, stage 640 may also include calculating and adjusting the current value of a derivative at a time before the final payout date, using either a formula based on the progress to date toward the specified payout goal(s), or by letting the market set the value according to the bids and offers from buyers wishing to purchase the derivative. Other ways of adjusting the value are also possible, within the scope of the invention.

One of ordinary skill in the art will recognize that process 600 depicted in FIG. 6 is an exemplary, generalized illustration and that stages and features may be added to, removed from, or modified within process 600 without departing from the principles of the invention. For example, a stage may be added to process 600 wherein the adjusted value of the derivative security is paid to holders of the derivative, as of the final payout date.

Health Care Credit Flows Derivatives

As explained in the related applications, which are incorporated by reference, in various embodiments, HCCs are transferable between a wide range of entities. Although HCCs may be created and awarded by different creating entities (e.g., by different insurance companies), in various embodiments, each creating entity honor HCCs created by another creating entity and/or the HCCs of different creating entities may be exchanged for each other, or bought and sold with cash, on exchanges or other marketplaces.

Figure 7:
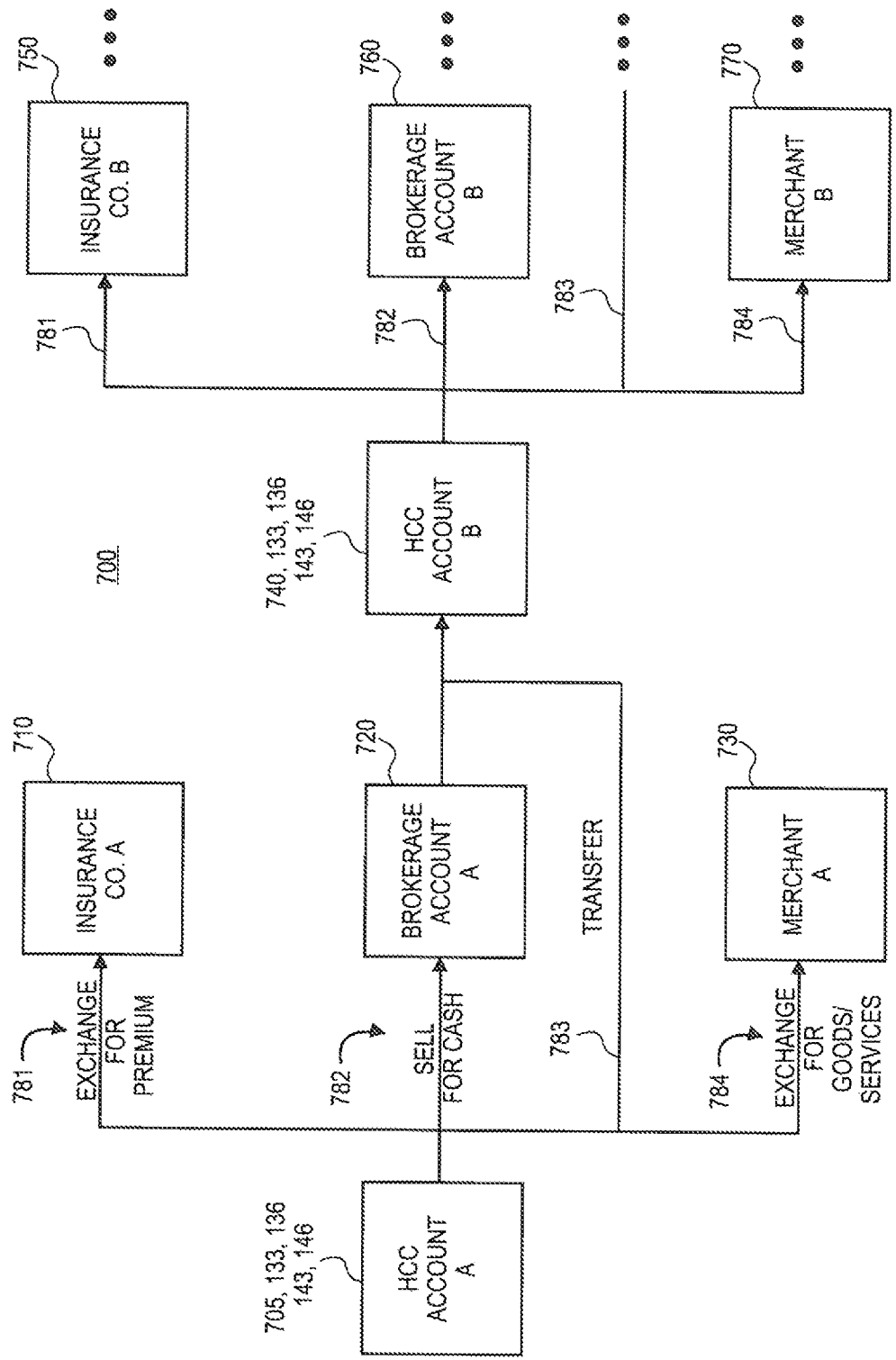
FIG. 7 is a block diagram showing an exemplary system for transferring and exchanging health care credits, consistent with the principles of the invention.

FIG. 7 is a block diagram showing an exemplary system 700 for transferring and exchanging health care credits, consistent with the principles of the invention. In the embodiment shown, HCC account A 705 contains HCC credits. HCC account A 705 may be, for example, a health care provider HCC account 133, a patient HCC account 136, or an individual HCC account 143 or 146.

The entity controlling HCC account A 705, such as an individual who has been awarded HCCs from his health insurer for achieving positive health outcomes, may freely transfer the HCCs to other entities in the HCC system 700. For example, an individual may transfer 781 HCCs from HCC account A 705 to a health insurance company A 710 in exchange for a reduction in the premium paid by the individual for health insurance.

Similarly, the individual may transfer 784 HCCs from HCC account A 705 to a merchant A 730 in exchange for goods and/or services provided by merchant A 730. In some embodiments, merchant A 730 may have contracted with health insurance company A 710 (or other entity creating or backing HCCs) to accept HCCs from customers in lieu of cash, with the arrangement that health insurance company A 710 will compensate merchant A 730 with cash for the accepted HCCs. In other embodiments, merchant A 730 may have no contract with health insurance company A 710, and may simply sell received HCCs for cash in a market such as HCC exchange 340 as described above with respect to FIG. 3. Other arrangements may also be used.

The controlling individual may also transfer 782 HCCs from HCC account A 705 to a brokerage account A 720, and then sell them for cash from brokerage account A 720 on a market such as HCC exchange 340 as described above with respect to FIG. 3.

As also shown in the embodiment of FIG. 7, the controlling individual may also directly transfer 783 HCCs from HCC account A 705 to an HCC account B 740, which may be, for example, a health care provider HCC account 133, a patient HCC account 136, or an individual HCC account 143 or 146. For instance, the controlling individual may transfer 783 HCCs as a gift to an account belonging to a family member.

As represented by the pathways 781, 782, 783, and 784 emanating from HCC account B 740, the entity controlling HCC account B 740 may similarly exchange, sell, or transfer the credits in the account for a variety of purposes. Thus, in various embodiments, HCCs are freely transferable among the accounts and entities of HCC system 700.

One of ordinary skill in the art will recognize that system 700 depicted in FIG. 7 is an exemplary, generalized illustration and that components and features may be added to, removed from, or modified within system 700 without departing from the principles of the invention. For example, one of ordinary skill will recognize that any number of merchants, insurance companies, brokerage accounts, individual accounts, exchanges, etc. may be added to system 700 without departing from the principles of the invention.

As exhibited by system 700, embodiments that report and store HCC account data may track the flow of HCCs throughout system 700, as each account records HCC transfers into and out of the account. And, there may be useful meanings attributed to each HCC transfer or flow. For example, HCC flows into certain accounts may indicate healthy people earning credits, HCC flows out of certain accounts may indicate people who require little health care are selling credits or exchanging credits for good and services, HCC flows into and out of other specific accounts may indicate unhealthy people buying credits and using them for healthcare services; etc.

Moreover, information regarding flow trends and quantities of HCCs being transferred to and/or from certain entities, such as to specific vendors (e.g., American Airlines or Wal-Mart), may be significant to investors who wish to make investments based on anticipated effects, or the predictive qualities, of the HCC flows.

Figure 8:
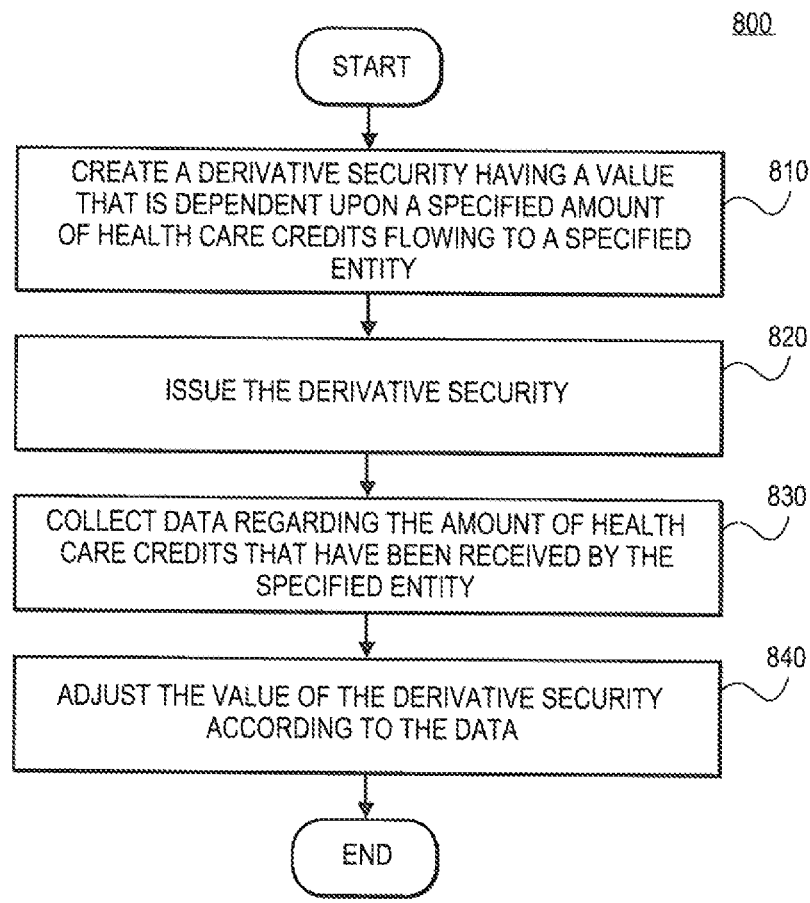
FIG. 8 is a flowchart of an exemplary process for managing a derivative security related to the transfer of health care credits, consistent with the principles of the invention.

FIG. 8 is a flowchart of an exemplary process 800 for managing a derivative security related to health care credits consistent with the principles of the invention, and in particular a derivative related to the flow of credits from and to various entities. In various embodiments, process 600 may be implemented using a computing system by an entity that is creating and/or managing derivates that are based on health care treatment and outcome data, such as HC derivative administrator 540, as shown in FIG. 5.

In the embodiment shown in FIG. 8, process 800 begins with creating a derivative security having a value that is dependent upon a specified amount of health care credits flowing to a specified entity (stage 810). For example, HC derivatives (similar to HC derivatives 551-554 of FIG. 5) may be created that increase in value, or pay out a specified amount, if a specified amount of HCCs flow into/out of the account(s) of a specified entity(ies), as indicated by the underlying HC data 515. In various embodiments, creating the derivative may include specifying a definite time(s) for achieving the specified amount(s) flowing to the specified entity(ies) or account(s), and specifying a definite payout(s) if the specified amount(s) are achieved at the specified time(s).

At stage 820, process 800 issues the derivative security to an investor(s). In some embodiments, this stage may be implements by selling or trading the HC derivative security either on a regulated exchange, such as the Chicago Board of Trade, on a custom HC exchange, such as HC 340 of FIG. 3, or off the exchanges, directly between the different counterparties.

Next, process 800 collects data regarding the amount of HCCs that have been received (or transmitted) by the specified entity(ies), which are the HCC flow(s) that underlies the derivative (stage 830). In various embodiments, the data collection of stage 830 may be ongoing over the life of the derivative, as new HCC flow data 565 is generated by account providers 560 over time. As shown in FIG. 5, process 800 may collect the relevant data by accessing data repository 520, which stores the HCC flow data 565 placed there by account providers 560.

At stage 840, process 800 adjusts the value of the derivative security according to the data collected in stage 840 and then ends. For HCC flow derivatives that feature a final payout at a specified ending date, this stage may involve analyzing the HCC flow data 565 collected in stage 830 as of the final payout date and determining whether or which payout conditions were met, in a manner similar to that described with respect to stage 640 of FIG. 6. For example, the value of a HCC flow derivative may be tied to a condition(s) that is discernable from health care data and HCC flow data that is generated and collected incidental to providing health care services and HCC transaction services to individuals and/or tied to whether/how that condition(s) is fulfilled or achieved. In various embodiments, stage 840 may also include calculating and adjusting the current value of a HCC flow derivative before the final payout date, using either a formula based on the progress to date toward the specified payout goal(s), or by letting the market set the value according to the bids and offers from buyers wishing to purchase the derivative.

One of ordinary skill in the art will recognize that process 800 depicted in FIG. 8 is an exemplary, generalized illustration and that stages and features may be added to, removed from, or modified within process 800 without departing from the principles of the invention. For example, a stage may be added to process 800 wherein the adjusted value of the derivative security is paid to holders of the derivative, as of the final payout date.

HCC Computing Systems

Figure 9:
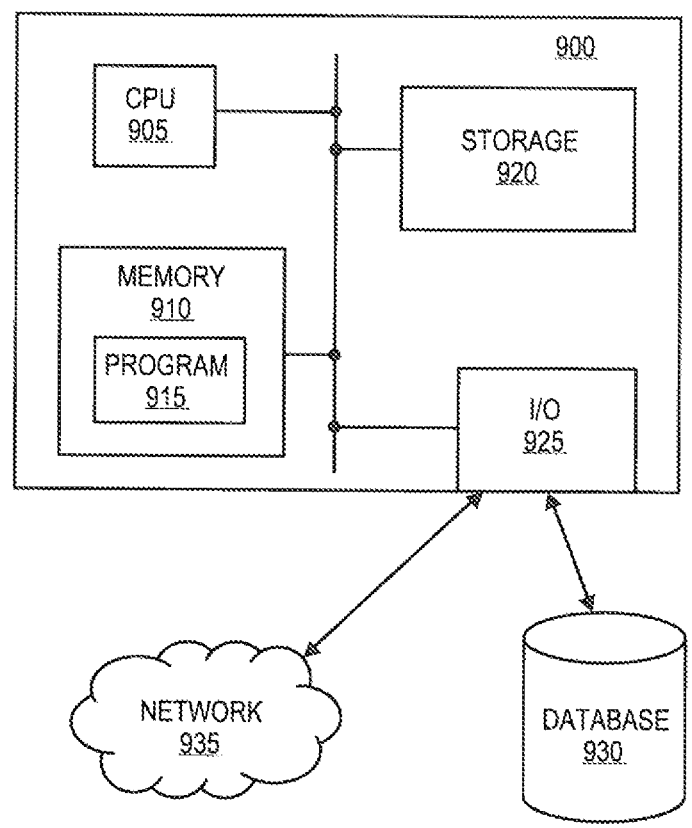
FIG. 9 is a block diagram illustrating an exemplary computing system suitable for implementing embodiments consistent with the principles of the invention.

FIG. 9 is a block diagram illustrating an exemplary computing system 900 suitable for implementing embodiments consistent with the principles of the invention. Other components and/or arrangements may also be used. In various embodiments, computing system 900, or several communicatively connected instances of computing system 900, may be used to implement processes 200, 400, 600, and 800, as well as HCC accounts, HCC exchange 340, and/or HC derivative administrator 540, among other things.

Computing system 900 includes a number of components, such as a central processing unit (CPU) 905, a memory 910, an input/output (I/O) device(s) 925, and a nonvolatile storage device 920. System 900 can be implemented in various ways. For example, an implementation as an integrated platform (such as a workstation, server, personal computer, laptop, smartphone, etc.) may comprise CPU 905, memory 910, nonvolatile storage 920, and I/O devices 925. In such a configuration, components 905, 910, 920, and 925 may connect and communicate through a local data bus and may access a database 930 (implemented, for example, as a separate database system) via an external I/O connection. I/O component(s) 925 may connect to external devices through a direct communication link (e.g., a hardwired or local wifi connection), through a network, such as a local area network (LAN) or a wide area network (WAN), and/or through other suitable connections. System 900 may be standalone or it may be a subsystem of a larger system.

CPU 905 may be one or more known processing devices, such as a microprocessor from the Core™ 2 family manufactured by the Intel™ Corporation of Santa Clara, Calif. Memory 910 may be one or more fast storage devices configured to store instructions and information used by CPU 905 to perform certain functions, methods, and processes related to embodiments of the present invention. Storage 920 may be a volatile or non-volatile, magnetic, semiconductor, tape, optical, or other type of storage device or computer-readable medium, including devices such as CDs and DVDs, meant for long-term storage.

In the illustrated embodiment, memory 910 contains one or more programs or subprograms 915 loaded from storage 920 or from a remote system (not shown) that, when executed by CPU 905, perform various operations, procedures, processes, or methods consistent with the present invention. Alternatively, CPU 905 may execute one or more programs located remotely from system 900. For example, system 900 may access one or more remote programs via network 935 that, when executed, perform functions and processes related to embodiments of the present invention.

In one embodiment, memory 910 may include a program(s) 915 that implements processes 200 and/or 400 and/or a program 915 that implements processes 600 and/or 800. In some embodiments, memory 910 may also include other programs or applications that implement other methods and processes that provide ancillary functionality to the invention. For example, memory 910 may include programs that gather, organize, store, and/or provide access to health care related data, such as HC data 515 and/or HCC flow data 565.

Memory 910 may be also be configured with other programs (not shown) unrelated to the invention and/or an operating system (not shown) that performs several functions well known in the art when executed by CPU 905. By way of example, the operating system may be Microsoft Windows™, Unix™, Linux™, an Apple Computers™ operating system, Personal Digital Assistant operating system such as Microsoft CE™, or other operating system. The choice of operating system, and even to the use of an operating system, is not critical to the invention.

I/O device(s) 925 may comprise one or more input/output devices that allow data to be received and/or transmitted by system 900. For example, I/O device 925 may include one or more input devices, such as a keyboard, touch screen, mouse, and the like, that enable data to be input from an administrative user, such as a system operator. Further, I/O device 525 may include one or more output devices, such as a display screen, CRT monitor, LCD monitor, plasma display, printer, speaker devices, and the like, that enable data to be output or presented to a user. I/O device 925 may also include one or more digital and/or analog communication input/output devices that allow computing system 900 to communicate, for example, digitally, with other machines and devices. Other configurations and/or numbers of input and/or output devices may be incorporated in I/O device 925.

In the embodiment shown, system 900 is connected to a network 935 (such as the Internet, a private network, a virtual private network, or other network), which may in turn be connected to various systems and computing machines (not shown), such as personal computers, laptop computers, servers, and/or smartphones of users 310. In general, system 900 may input data from external machines and devices and output data to external machines and devices via network 935.

In the exemplary embodiment shown in FIG. 9, database 930 is a standalone database external to system 900. In other embodiments, database 930 may be hosted by system 900. In various embodiments, database 930 may manage and store data used to implement systems and methods consistent with the invention. For example, database 930 may manage and store data structures that contain data such as HC data 515 and/or HCC flow data 565.

Database 930 may comprise one or more databases that store information and are accessed and/or managed through system 900. By way of example, database 930 may be an Oracle™ database, a Sybase™ database, or other relational database. Systems and methods consistent with the invention, however, are not limited to separate data structures or databases, or even to the use of a database or data structure.

The preceding description of a computing system is exemplary and not meant to be limiting. In one or more exemplary implementations, the functions and processes described may be implemented in hardware, software, firmware, or any combination thereof. If implemented in software, the functions may be stored as instructions or code on a computer-readable medium. Computer-readable media includes both computer storage media and communication media including any medium that facilitates transfer of a computer program from one place to another. A storage media may be any available non-transitory media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to hold desired program code in the form of instructions or data structures and that can be accessed by a computer. Also, any remote device may be properly termed a computer-readable medium. Combinations of the elements described herein can also be included within the scope of computer-readable media.

The processing of a method, process, or algorithm described in connection with the implementations disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. In some embodiments, the storage medium may be integral to the processor. The processor and the storage medium may reside in an ASIC. The ASIC may reside in a computing device or computing system.

Other embodiments of the invention will be apparent to those skilled in the art from consideration of the specification and practice of the invention disclosed herein. For example, in some embodiments, the computing systems and/or software that implements the described systems and methods may deployed in a cloud. For another example, various embodiments may be combined with social networking features, such as awarding or earning HCCs for causing social network contacts (e.g., friends) to engage in health-beneficial behavior (e.g., visiting a health food website or exercise equipment website and making a purchase). Accordingly, it is intended that the specification and examples be considered as exemplary only, with a true scope and spirit of the invention being indicated by the following claims.

What is claimed is:

1. A method, implemented using a computing system, of managing a health care credit, the method comprising:
    receiving a freely transferrable non-monetary consideration that represents good health, or improvement in health, or maintenance of health;
    storing, using the computing system, the freely transferrable non-monetary consideration in an account controlled by an entity;
    calculating, using the computing system, a current value of the account according to a market value of the freely transferrable non-monetary consideration from a health care credit exchange that is a market that freely transfers the freely transferrable non-monetary consideration between and among entities;
    storing the current value of the account in the account;
    receiving an instruction from the entity; and
    deducting, using the computing system, a portion of the freely transferrable non-monetary consideration from the account according to the instruction.

2. The method of claim 1, further comprising:
    transferring the portion of the freely transferrable non-monetary consideration to a second account controlled by a second entity.

3. The method of claim 2, further comprising:
    receiving an amount of money equivalent to a current market value of the portion of the non-monetary consideration, wherein the current market value of the portion is based on a price from the health care credit exchange.

4. The method of claim 1, further comprising:
    transferring money to a second entity; and
    receiving, for the money, a second freely transferrable non-monetary consideration that represents good health, or improvement in health, or maintenance of health.

5. The method of claim 1, wherein receiving the instruction from the entity comprises:
    receiving an instruction to sell the portion of the freely transferrable non-monetary consideration for a specified minimum price.

6. The method of claim 1, wherein receiving the instruction from the entity comprises:
    receiving an instruction to sell the portion of the freely transferrable non-monetary consideration for a market price from the health care credit exchange.

7. The method of claim 1, wherein receiving the freely transferrable non-monetary consideration comprises:
    receiving the freely transferrable non-monetary consideration from a health insurer.

8. The method of claim 1, further comprising:
    storing, in association with the account, data reflecting the good health, the improvement in health, or the maintenance of health represented by the freely transferrable non-monetary consideration.

9. The method of claim 1, wherein an insurance premium is reduced in exchange for the portion of the freely transferrable non-monetary consideration that was deducted.

10. The method of claim 1, wherein receiving the instruction from the entity comprises:
    receiving an instruction to sell the portion of the freely transferrable non-monetary consideration; and
    wherein the method further comprises:
    offering the portion of the freely transferrable non-monetary consideration for sale on the health care credit exchange.

11. The method of claim 1, wherein the freely transferrable non-monetary consideration is a security.

12. The method of claim 1, wherein the freely transferrable non-monetary consideration is electronic data representing a freely transferrable non-monetary asset.

13. A method, implemented using a computing system, of managing an account, the method comprising:
    receiving a health care credit, wherein the health care credit represents good health, or improvement in health, or maintenance of health, and wherein the health care credit is a freely transferrable non-monetary consideration;
    obtaining a market value of the health care credit from a health care credit exchange that is a market where health care credits are bought and sold;
    calculating, using the computing system, a value of the account according to the market value of the health care credit from the health care credit exchange;

storing, using the computing system, the health care credit and the value of the account in the account, wherein the account is controlled by an entity;

receiving an instruction from the entity; and deducting, using the computing system, the health care credit from the account according to the instruction.

14. The method of claim 13, further comprising:
transferring the health care credit to a second account controlled by a second entity.

15. The method of claim 14, further comprising:
receiving an amount of money equivalent to a current market value of the health care credit that was transferred, wherein the current market value of the health care credit is based on a price from the health care credit exchange.

16. The method of claim 13, further comprising:
transferring money to a second entity; and
receiving, for the money, a second health care credit.

17. The method of claim 13, wherein receiving the instruction from the entity comprises:
receiving an instruction to sell the health care credit for a specified minimum price.

18. The method of claim 13, wherein receiving the instruction from the entity comprises:
receiving an instruction to sell the health care credit for a market price from the health care credit exchange.

19. The method of claim 13, wherein receiving the health care credit comprises:
receiving the health care credit from a health insurer as an award for good health, an improvement in health, or maintenance of health.

20. The method of claim 13, further comprising:
storing, in association with the account, data reflecting the good health, the improvement in health, or the maintenance of health represented by the health care credit.

21. The method of claim 13, wherein an insurance premium is reduced in exchange for the health care credit that was deducted.

22. The method of claim 13, wherein receiving the instruction from the entity comprises:
receiving an instruction to sell the health care credit; and
wherein the method further comprises:
enabling an offering of the health care credit for sale on the health care credit exchange.

23. The method of claim 13, wherein the health care credit is a freely transferrable security.

24. The method of claim 13, wherein the health care credit is electronic data representing a freely transferrable non-monetary asset.

25. A method, implemented using a computing system, of managing an account controlled by an entity, the method comprising:
receiving a health care credit, wherein the health care credit represents good health, or improvement in health, or maintenance of health, and wherein the health care credit is a freely transferrable non-monetary consideration;

calculating, using the computing system, a value of the account according to the market value of the health care credit from a health care credit exchange that is a market where health care credits are bought and sold;

storing, using the computing system, the health care credit and the value of the account in association with the account;

transferring, using the computing system, the health care credit out of the account.

26. The method of claim 25, wherein transferring the health care credit out of the account further comprises:
transferring the health care credit to a second account controlled by a second entity.

27. The method of claim 26, further comprising:
receiving money from the second entity in exchange for the health care credit that was transferred.

28. The method of claim 25, further comprising:
transferring money to a second entity; and
receiving, for the money, a second health care credit.

29. The method of claim 25, further comprising:
receiving an instruction from the entity to sell the health care credit for a specified minimum amount of money.

30. The method of claim 25, further comprising:
receiving an instruction from the entity to sell the health care credit for a market price gotten from the health care credit exchange.

31. The method of claim 25, wherein receiving the health care credit comprises:
receiving the health care credit from a health insurer.

32. The method of claim 25, further comprising:
storing, in association with the account, data describing the good health, the improvement in health, or the maintenance of health represented by the health care credit.

33. The method of claim 25, wherein an insurance premium is reduced in exchange for the health care credit that was transferred.

34. The method of claim 25, further comprising:
receiving an instruction from the entity to sell the health care credit; and
enabling an offering of the health care credit for sale on the health care credit exchange.

35. The method of claim 25, wherein the health care credit is a freely transferrable security.

36. The method of claim 25, wherein the health care credit is electronic data representing a freely transferrable non-monetary asset.

37. An apparatus, the apparatus comprising:
a memory containing instructions; and
a processor, operably connected to the memory, that executes the instructions to perform operations comprising:
receiving a freely transferrable non-monetary consideration that represents good health, or improvement in health, or maintenance of health;
storing the freely transferrable non-monetary consideration in an account controlled by an entity;
calculating a current value of the account according to a market value of the freely transferrable non-monetary consideration from a health care credit exchange that is a market that freely transfers the freely transferrable non-monetary consideration between and among entities;
storing the current value of the account in the account;
receiving an instruction from the entity; and
deducting a portion of the freely transferrable non-monetary consideration from the account according to the instruction.

38. The apparatus of claim 37, wherein the operations further comprise:
transferring the portion of the freely transferrable non-monetary consideration to a second account controlled by a second entity.

39. The apparatus of claim 37, wherein the operations further comprise:
receiving an amount of money equivalent to a current market value of the portion of the non-monetary consideration, wherein the current market value of the portion is based on a price from the health care credit exchange.

40. The apparatus of claim 37, wherein the operations further comprise:
transferring money to a second entity; and
receiving, for the money, a second freely transferrable non-monetary consideration that represents good health, or improvement in health, or maintenance of health.

41. The apparatus of claim 37, wherein receiving the instruction from the entity comprises:
receiving an instruction to sell the portion of the freely transferrable non-monetary consideration for a specified minimum price.

42. The apparatus of claim 37, wherein receiving the instruction from the entity comprises:
receiving an instruction to sell the portion of the freely transferrable non-monetary consideration for a market price from the health care credit exchange.

43. The apparatus of claim 37, wherein receiving the freely transferrable non-monetary consideration comprises:
receiving the freely transferrable non-monetary consideration from a health insurer.

44. The apparatus of claim 37, wherein the operations further comprise:
storing, in association with the account, data reflecting the good health, the improvement in health, or the maintenance of health represented by the freely transferrable non-monetary consideration.

45. The apparatus of claim 37, wherein an insurance premium is reduced in exchange for the portion of the freely transferrable non-monetary consideration that was deducted.

46. The apparatus of claim 37, wherein receiving the instruction from the entity comprises:
receiving an instruction to sell the portion of the freely transferrable non-monetary consideration; and
wherein the operations further comprise:
offering the portion of the freely transferrable non-monetary consideration for sale on the health care credit exchange.

47. The apparatus of claim 37, wherein the freely transferrable non-monetary consideration is a security.

48. The apparatus of claim 37, wherein the freely transferrable non-monetary consideration is electronic data representing a freely transferrable non-monetary asset.

49. An apparatus, the apparatus comprising:
a memory containing instructions; and
a processor, operably connected to the memory, that executes the instructions to perform operations comprising:
receiving a health care credit, wherein the health care credit represents good health, or improvement in health, or maintenance of health, and wherein the health care credit is a freely transferrable non-monetary consideration;
obtaining a market value of the health care credit from a health care credit exchange that is a market where health care credits are bought and sold;
calculating a value of the account according to the market value of the health care credit from the health care credit exchange;
storing the health care credit and the value of the account in the account, wherein the account is controlled by an entity;
receiving an instruction from the entity; and
deducting the health care credit from the account according to the instruction.

50. The apparatus of claim 49, wherein the operations further comprise:
transferring the health care credit to a second account controlled by a second entity.

51. The apparatus of claim 50, wherein the operations further comprise:
receiving an amount of money equivalent to a current market value of the health care credit that was transferred, wherein the current market value of the health care credit is based on a price from the health care credit exchange.

52. The apparatus of claim 49, wherein the operations further comprise:
transferring money to a second entity; and
receiving, for the money, a second health care credit.

53. The apparatus of claim 49, wherein receiving the instruction from the entity comprises:
receiving an instruction to sell the health care credit for a specified minimum price.

54. The apparatus of claim 49, wherein receiving the instruction from the entity comprises:
receiving an instruction to sell the health care credit for a market price from the health care credit exchange.

55. The apparatus of claim 49, wherein receiving the health care credit comprises:
receiving the health care credit from a health insurer as an award for good health, an improvement in health, or maintenance of health.

56. The apparatus of claim 49, wherein the operations further comprise:
storing, in association with the account, data reflecting the good health, the improvement in health, or the maintenance of health represented by the health care credit.

57. The apparatus of claim 49, wherein an insurance premium is reduced in exchange for the health care credit that was deducted.

58. The apparatus of claim 49, wherein receiving the instruction from the entity comprises:
receiving an instruction to sell the health care credit; and
wherein the method further comprises:
enabling an offering of the health care credit for sale on the health care credit exchange.

59. The apparatus of claim 49, wherein the health care credit is a freely transferrable security.

60. The apparatus of claim 49, wherein the health care credit is electronic data representing a freely transferrable non-monetary asset.

61. An apparatus, the apparatus comprising:
a memory containing instructions; and
a processor, operably connected to the memory, that executes the instructions to perform operations comprising:
receiving a health care credit, wherein the health care credit represents good health, or improvement in health, or maintenance of health, and wherein the health care credit is a freely transferrable non-monetary consideration;
calculating a value of the account according to the market value of the health care credit from a health care credit exchange that is a market where health care credits are bought and sold;
storing the health care credit and the value of the account in association with the account;
transferring the health care credit out of the account.

62. The apparatus of claim 61, wherein transferring the health care credit out of the account further comprises:
transferring the health care credit to a second account controlled by a second entity.

63. The apparatus of claim 62, wherein the operations further comprise:
receiving money from the second entity in exchange for the health care credit that was transferred.

64. The apparatus of claim 61, wherein the operations further comprise:
transferring money to a second entity; and
receiving, for the money, a second health care credit.

65. The apparatus of claim 61, wherein the operations further comprise:
receiving an instruction from the entity to sell the health care credit for a specified minimum amount of money.

66. The apparatus of claim 61, wherein the operations further comprise:
receiving an instruction from the entity to sell the health care credit for a market price gotten from the health care credit exchange.

67. The apparatus of claim 61, wherein receiving the health care credit comprises:
receiving the health care credit from a health insurer.

68. The apparatus of claim 61, wherein the operations further comprise:
storing, in association with the account, data describing the good health, the improvement in health, or the maintenance of health represented by the health care credit.

69. The apparatus of claim 61, wherein an insurance premium is reduced in exchange for the health care credit that was transferred.

70. The apparatus of claim 61, wherein the operations further comprise:
receiving an instruction from the entity to sell the health care credit; and
enabling an offering of the health care credit for sale on the health care credit exchange.

71. The apparatus of claim 61, wherein the health care credit is a freely transferrable security.

72. The apparatus of claim 61, wherein the health care credit is electronic data representing a freely transferrable non-monetary asset.

73. A non-transitory computer-readable medium containing instruction that, when executed by a processor, perform operations comprising:
receiving a freely transferrable non-monetary consideration that represents good health, or improvement in health, or maintenance of health;
storing the freely transferrable non-monetary consideration in an account controlled by an entity;
calculating a current value of the account according to a market value of the freely transferrable non-monetary consideration from a health care credit exchange that is a market that freely transfers the freely transferrable non-monetary consideration between and among entities;
storing the current value of the account in the account;
receiving an instruction from the entity; and
deducting a portion of the freely transferrable non-monetary consideration from the account according to the instruction.

74. The computer-readable medium of claim 73, wherein the operations further comprise:
transferring the portion of the freely transferrable non-monetary consideration to a second account controlled by a second entity.

75. The computer-readable medium of claim 74, wherein the operations further comprise:
receiving an amount of money equivalent to a current market value of the portion of the non-monetary consideration, wherein the current market value of the portion is based on a price from the health care credit exchange.

76. The computer-readable medium of claim 73, wherein the operations further comprise:
transferring money to a second entity; and
receiving, for the money, a second freely transferrable non-monetary consideration that represents good health, or improvement in health, or maintenance of health.

77. The computer-readable medium of claim 73, wherein receiving the instruction from the entity comprises:
receiving an instruction to sell the portion of the freely transferrable non-monetary consideration for a specified minimum price.

78. The computer-readable medium of claim 73, wherein receiving the instruction from the entity comprises:
receiving an instruction to sell the portion of the freely transferrable non-monetary consideration for a market price from the health care credit exchange.

79. The computer-readable medium of claim 73, wherein receiving the freely transferrable non-monetary consideration comprises:
receiving the freely transferrable non-monetary consideration from a health insurer.

80. The computer-readable medium of claim 73, wherein the operations further comprise:
storing, in association with the account, data reflecting the good health, the improvement in health, or the maintenance of health represented by the freely transferrable non-monetary consideration.

81. The computer-readable medium of claim 73, wherein an insurance premium is reduced in exchange for the portion of the freely transferrable non-monetary consideration that was deducted.

82. The computer-readable medium of claim 73, wherein receiving the instruction from the entity comprises:
receiving an instruction to sell the portion of the freely transferrable non-monetary consideration; and
wherein the operations further comprise:
offering the portion of the freely transferrable non-monetary consideration for sale on the health care credit exchange.

83. The computer-readable medium of claim 73, wherein the freely transferrable non-monetary consideration is a security.

84. The computer-readable medium of claim 73, wherein the freely transferrable non-monetary consideration is electronic data representing a freely transferrable non-monetary asset.

85. A non-transitory computer-readable medium containing instruction that, when executed by a processor, perform operations comprising:
receiving a health care credit, wherein the health care credit represents good health, or improvement in health, or maintenance of health, and wherein the health care credit is a freely transferrable non-monetary consideration;
obtaining a market value of the health care credit from a health care credit exchange that is a market where health care credits are bought and sold;
calculating a value of the account according to the market value of the health care credit from the health care credit exchange;
storing the health care credit and the value of the account in the account, wherein the account is controlled by an entity;
receiving an instruction from the entity; and deducting the health care credit from the account according to the instruction.

86. The computer-readable medium of claim 85, wherein the operations further comprise:
transferring the health care credit to a second account controlled by a second entity.

87. The computer-readable medium of claim 86, wherein the operations further comprise:
receiving an amount of money equivalent to a current market value of the health care credit that was transferred, wherein the current market value of the health care credit is based on a price from the health care credit exchange.

88. The computer-readable medium of claim 85, wherein the operations further comprise:
transferring money to a second entity; and
receiving, for the money, a second health care credit.

89. The computer-readable medium of claim 85, wherein receiving the instruction from the entity comprises:
receiving an instruction to sell the health care credit for a specified minimum price.

90. The computer-readable medium of claim 85, wherein receiving the instruction from the entity comprises:
receiving an instruction to sell the health care credit for a market price from the health care credit exchange.

91. The computer-readable medium of claim 85, wherein receiving the health care credit comprises:
receiving the health care credit from a health insurer as an award for good health, an improvement in health, or maintenance of health.

92. The computer-readable medium of claim 85, wherein the operations further comprise:
storing, in association with the account, data reflecting the good health, the improvement in health, or the maintenance of health represented by the health care credit.

93. The computer-readable medium of claim 85, wherein an insurance premium is reduced in exchange for the health care credit that was deducted.

94. The computer-readable medium of claim 85, wherein receiving the instruction from the entity comprises:
receiving an instruction to sell the health care credit; and
wherein the operations further comprise:
enabling an offering of the health care credit for sale on the health care credit exchange.

95. The computer-readable medium of claim 85, wherein the health care credit is a freely transferrable security.

96. The computer-readable medium of claim 85, wherein the health care credit is electronic data representing a freely transferrable non-monetary asset.

97. A non-transitory computer-readable medium containing instruction that, when executed by a processor, perform operations comprising:
receiving a health care credit, wherein the health care credit represents good health, or improvement in health, or maintenance of health, and wherein the health care credit is a freely transferrable non-monetary consideration;
calculating a value of the account according to the market value of the health care credit from a health care credit exchange that is a market where health care credits are bought and sold;
storing the health care credit and the value of the account in association with the account;
transferring the health care credit out of the account.

98. The computer-readable medium of claim 97, wherein transferring the health care credit out of the account further comprises:
transferring the health care credit to a second account controlled by a second entity.

99. The computer-readable medium of claim 98, wherein the operations further comprise:
receiving money from the second entity in exchange for the health care credit that was transferred.

100. The computer-readable medium of claim 97, wherein the operations further comprise:
transferring money to a second entity; and
receiving, for the money, a second health care credit.

101. The computer-readable medium of claim 97, wherein the operations further comprise:
receiving an instruction from the entity to sell the health care credit for a specified minimum amount of money.

102. The computer-readable medium of claim 97, wherein the operations further comprise:
receiving an instruction from the entity to sell the health care credit for a market price gotten from the health care credit exchange.

103. The computer-readable medium of claim 97, wherein receiving the health care credit comprises:
receiving the health care credit from a health insurer.

104. The computer-readable medium of claim 97, wherein the operations further comprise:
storing, in association with the account, data describing the good health, the improvement in health, or the maintenance of health represented by the health care credit.

105. The computer-readable medium of claim 97, wherein an insurance premium is reduced in exchange for the health care credit that was transferred.

106. The computer-readable medium of claim 97, wherein the operations further comprise:
receiving an instruction from the entity to sell the health care credit; and
enabling an offering of the health care credit for sale on the health care credit exchange.

107. The computer-readable medium of claim 97, wherein the health care credit is a freely transferrable security.

108. The computer-readable medium of claim 97, wherein the health care credit is electronic data representing a freely transferrable non-monetary asset.

* * * * *